United States Patent
Nielsen et al.

(10) Patent No.: US 11,426,383 B2
(45) Date of Patent: *Aug. 30, 2022

(54) TESOFENSINE AND BETA BLOCKER COMBINATION FORMULATIONS

(71) Applicant: SANIONA A/S, Glostrup (DK)

(72) Inventors: Peter G. Nielsen, Vaerløse (DK); Mikael S. Thomsen, Hvidovre (DK); Bent Højgaard, Allerød (DK)

(73) Assignee: Saniona A/S, Glostrup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/066,843

(22) Filed: Oct. 9, 2020

(65) Prior Publication Data

US 2021/0023050 A1    Jan. 28, 2021

Related U.S. Application Data

(60) Continuation of application No. 16/705,370, filed on Dec. 6, 2019, now Pat. No. 10,828,278, which is a division of application No. 16/113,574, filed on Aug. 27, 2018, now Pat. No. 10,537,551, which is a continuation of application No. 15/554,449, filed as application No. PCT/DK2016/050058 on Mar. 2, 2016, now Pat. No. 10,231,951.

(30) Foreign Application Priority Data

Mar. 3, 2015   (DK) .................. PA 2015 70117
Oct. 9, 2015   (DK) .................. PA 2015 70644

(51) Int. Cl.
| A61K 31/403 | (2006.01) |
|---|---|
| A61K 31/138 | (2006.01) |
| A61K 31/46 | (2006.01) |
| A61K 9/20 | (2006.01) |
| A61K 9/24 | (2006.01) |
| A61K 9/28 | (2006.01) |
| A61K 45/06 | (2006.01) |

(52) U.S. Cl.
CPC ............ *A61K 31/403* (2013.01); *A61K 9/209* (2013.01); *A61K 9/2013* (2013.01); *A61K 9/2054* (2013.01); *A61K 9/2081* (2013.01); *A61K 9/282* (2013.01); *A61K 9/2846* (2013.01); *A61K 31/138* (2013.01); *A61K 31/46* (2013.01); *A61K 45/06* (2013.01)

(58) Field of Classification Search
CPC ...... A61K 31/138; A61K 31/46; A61K 9/209; A61K 9/1676; A61P 3/04
See application file for complete search history.

(56) References Cited

U.S. PATENT DOCUMENTS

| 5,885,616 A | 3/1999 | Hsiao et al. |
|---|---|---|
| 7,314,640 B2 * | 1/2008 | Sriwongjanya ........ A61K 31/00 424/490 |
| 7,959,947 B2 | 6/2011 | Hoelzer et al. |
| 8,101,209 B2 | 1/2012 | Legrand et al. |
| 2004/0058001 A1 | 3/2004 | Hoelzer et al. |
| 2004/0127515 A1 | 7/2004 | Murugesan et al. |
| 2007/0202172 A1 | 8/2007 | Gold et al. |
| 2009/0068260 A1 | 3/2009 | Gold et al. |
| 2010/0305213 A1 | 12/2010 | Beddies et al. |
| 2011/0020460 A1 | 1/2011 | Mascitti et al. |
| 2011/0217374 A1 | 9/2011 | Oh et al. |
| 2013/0251793 A1 | 9/2013 | Fanda et al. |
| 2013/0252973 A1 | 9/2013 | Pfefferkorn et al. |
| 2015/0025107 A1 | 1/2015 | Hansen et al. |

FOREIGN PATENT DOCUMENTS

| CN | 102626396 A | 8/2012 | |
|---|---|---|---|
| DE | 102006020604 A1 | 11/2007 | |
| JP | 2004-522741 A | 7/2004 | |
| JP | 2009-527554 A | 7/2009 | |
| JP | 2013-507356 A | 3/2013 | |
| WO | 92/16197 A1 | 10/1992 | |
| WO | 97/30997 A1 | 8/1997 | |
| WO | 02/58677 A1 | 8/2002 | |
| WO | 03/00256 A1 | 1/2003 | |
| WO | 03/74500 | 9/2003 | |
| WO | 2004/069234 A1 | 8/2004 | |
| WO | 2004/096810 A1 | 11/2004 | |
| WO | 2005/070427 A1 | 8/2005 | |
| WO | 2007/029070 A1 | 3/2007 | |
| WO | 2007/048233 A1 | 5/2007 | |
| WO | 2007/097770 A1 | 8/2007 | |
| WO | 2007/110753 A2 | 10/2007 | |
| WO | 2008/012346 A1 | 1/2008 | |
| WO | 2009/065845 A1 | 5/2009 | |
| WO | 2009/080691 A2 | 7/2009 | |
| WO | 2009/080693 A2 | 7/2009 | |
| WO | WO-2009080693 A2 * | 7/2009 | ............. A61K 31/46 |
| WO | 2011/049309 A2 | 4/2011 | |
| WO | 2011/051864 A1 | 5/2011 | |
| WO | 2011/100659 A2 | 8/2011 | |
| WO | 2011/143420 A1 | 11/2011 | |
| WO | 2012/052834 A2 | 4/2012 | |

(Continued)

OTHER PUBLICATIONS

Gilbert, Obesity, 20, 2012 (Year: 2012).*

(Continued)

*Primary Examiner* — Susan T Tran
*Assistant Examiner* — William Craigo
(74) *Attorney, Agent, or Firm* — BakerHostetler

(57) ABSTRACT

The present invention relates to a controlled release formulation comprising the active compounds tesofensine and a beta blocker, such as metoprolol or carvedilol, or a pharmaceutically acceptable salt thereof. The invention further relates to use of the controlled release formulation in a method of treatment of diabetes, obesity, or an obesity associated disorder.

17 Claims, 4 Drawing Sheets

(56) References Cited

FOREIGN PATENT DOCUMENTS

| WO | 2012/154563 | A1 | | 11/2012 | |
|---|---|---|---|---|---|
| WO | 2013/001516 | A1 | | 1/2013 | |
| WO | 2013/030725 | A1 | | 3/2013 | |
| WO | 2013/084089 | A1 | | 6/2013 | |
| WO | 2013/120935 | A1 | | 8/2013 | |
| WO | WO-2013120935 | A1 | * | 8/2013 | ............... A61P 9/10 |
| WO | 2015/004617 | A1 | | 1/2015 | |

OTHER PUBLICATIONS

Rajendran, IJPSR, 2, 12, 2011 (Year: 2011).*
Astrup et al. "Effect of tesofensine on bodyweight loss, body composition, and quality of life in obese patients: a randomized, double-blind, placebo-controlled trial", The Lancet, Nov. 29, 2008, vol. 372, No. 9653, 1906-1913.
Astrup et al., "Weight Loss Produced by Tesofensine in patients with Parkinson's or Alzheimer's Disease", Obesity, Jun. 1, 2008, vol. 16, No. 6, 1363-1369.
Axel et al., "Tesofensine, a Novel Triple Monoamine Reuptake Inhibitor, Induces Appetite Suppression by Indirect Stimulation of $\alpha_I$ Adrenoceptor and Dopamine $\beta_I$ Receptor Pathways in the Diet-Induced Obese Rat", Neuropsychopharmacology, Mar. 3, 2010, 35, 1464-1476.
Bara-Jimenez W, et al., Mouradian MM, Chase TN (2004). "Effect of monoamine reuptake inhibitor NS 2330 in advanced Parkinson's disease". Mov Disord 19 (10): 1183-6.
Bentzen et al., "Anti-hypertensive treatment preserves appetite suppression while preventing cardiovascular adverse effects of tesofensine in rats", Obesity, May 2013, vol. 21, No. 5, 985-992.
Gondoni et al., "Effect of chronic treatment with beta-blockers on resting energy expenditure in obese hypertensive patients during a low-calorie and physical training program", NMCD, Nutrition Metabolism and Cardiovascular Diseases, Aug. 2003, vol. 13, No. 4, 232-237.
Grundy, Journal of the American College of Cardiology, 59, 7, 2012 (Year: 2012).
International Patent Application No. PCT/DK2016/050058: International Search Report and Written Opinion dated May 14, 2016, 11 pages.
International Patent Application No. PCT/EP2013/052941: International Search Report dated May 2, 2103, 3 pages.
Messerli et al., "Body Weight Changes with .beta.-Blocker Use: Results from Gemini", The American Journal of Medicine, Jul. 2007, 120, 610-615.

* cited by examiner

A+B+C

TESOFENSINE AND BETA BLOCKER COMBINATION FORMULATIONS

CROSS REFERENCE TO RELATED APPLICATIONS

This application is a continuation of U.S. application Ser. No. 16/705,370, filed Dec. 6, 2019, which is a divisional of U.S. application Ser. No. 16/113,574, filed Aug. 27, 2018, now U.S. Pat. No. 10,537,551, which is a continuation of U.S. application Ser. No. 15/554,449, filed Aug. 30, 2017, now U.S. Pat. No. 10,231,951, which is a national stage entry of International Application No. PCT/DK2016/050058, filed Mar. 2, 2016, which claims the benefit of Denmark Application Nos. PA 2015 70117, filed Mar. 3, 2015, and PA 2015 70644, filed Oct. 9, 2015, the entireties of which are incorporated herein in their entireties.

FIELD OF INVENTION

The present invention relates to a new controlled release formulations comprising the active compounds tesofensine and a beta blocker, such as metoprolol or carvedilol, or pharmaceutically acceptable salts thereof.

BACKGROUND OF INVENTION

Within the past decades the prevalence of obesity has risen in virtually all ethnic, racial and socioeconomic populations, in both genders and in all age groups. Obesity is associated with a significantly elevated risk for type 2 diabetes, coronary heart diseases, hypertension and numerous other major illnesses and overall mortality from all causes. Therefore, weight reduction is critical for the obese patient. Thus there is impetus for creating new and alternative treatments for management of obesity.

Tesofensine, i.e. [(1R,2R,3S,5S)-3-(3,4-dichlorophenyl)-2-(ethoxymethyl)-8-methyl-8-azabicyclo[3.2.1]octane], first described in WO 97/30997, is a triple monoamine reuptake inhibitor in development for the treatment of obesity.

Tesofensine effectively produces a weight loss in obese individuals of about twice of that seen with currently marketed anti-obesity drugs. Results from clinical studies with Tesofensine also showed that the compound has a good safety profile and is well tolerated. However, though no clinically relevant cardiovascular adverse events or changes in either blood pressure or pulse were seen, some cardiovascular effects were measured with slight increases in heart rate and trends in blood pressure. Although such small effects have no immediate risk to the patient, some medical and regulatory concerns have been raised based on observational studies, that even small changes in cardiovascular parameters may have long term implications on patients' benefit/risk evaluation.

Preclinical and clinical data suggest that appetite suppression is an important mechanism by which Tesofensine exerts its robust weight reducing effect. Notably, the strong hypophagic response (i.e. less appetite, decreased feeding) to Tesofensine treatment is demonstrated to be linked to central stimulation of noradrenergic and dopaminergic neurotransmission. However, the sympathomimetic mode of action of Tesofensine may also associate with the elevated heart rate and blood pressure observed in clinical settings.

Beta blockers, (β-blockers, beta-adrenergic blocking agents, beta antagonists, beta-adrenergic antagonists, beta-adrenoreceptor antagonists, or beta adrenergic receptor antagonists) are a class of drugs that are typically used for the management of cardiac arrhythmias, protecting the heart from a second heart attack (myocardial infarction) after a first heart attack (secondary prevention), and, in certain cases, hypertension. Beta blockers are also well known for their reductive effect on heart rate.

Metoprolol, i.e. 1-(Isopropylamino)-3-[4-(2-methoxyethyl)-phenoxy]-propan-2-ol, branded under various trade names, is a selective β1 (adrenergic) receptor blocker normally used in the treatment of various disorders of the cardiovascular system, and in particular hypertension.

Carvedilol ((±)-[3-(9H-carbazol-4-yloxy)-2-hydroxypropyl][2-(2-methoxyphenoxy)ethyl]amine) is a mixed, i.e. nonselective alpha and beta blocker. It is marketed under various trade names and is traditionally used in the treatment of mild to severe congestive heart failure (CHF) and high blood pressure.

WO 2013/120935 describes treatment of obesity by co-administration of tesofensine and metoprolol in order to ameliorate drug-induced elevation of blood pressure or increase in heart rate.

The serum half-life of tesofensine is nine days (Bara-Jimenez W, Dimitrova T, Sherzai A, Favit A, Mouradian M M, Chase T N (2004). "Effect of monoamine reuptake inhibitor NS 2330 in advanced Parkinson's disease". *Mov Disord* 19 (10): 1183-6). In comparison, the half-life of beta blockers is quite short with metoprolol in the order of 3-4 hours and carvedilol about 7 to 10 hours. Therefore simultaneous daily administration of these two drugs is likely to induce high fluctuations in the serum levels of the beta blocker and potentially recurrent temporary absence of therapeutic efficacy of the beta blocker.

SUMMARY OF DISCLOSURE

The present disclosure relates to pharmaceutical compositions comprising a. a first composition comprising an extended release composition of an active pharmaceutical ingredient (API) selected from a beta blocker or a pharmaceutically acceptable salt thereof, b. a second composition comprising active pharmaceutical ingredient (API) selected from tesofensine or a pharmaceutically acceptable salt thereof, and c. a third composition comprising an immediate release composition of an active pharmaceutical ingredient (API) selected from a beta blocker or a pharmaceutically acceptable salt thereof.

The pharmaceutical composition is effective in treating obesity without causing the undesired increase in heart rate and blood pressure observed for treatment with tesofensine alone. The release profiles of the three components of the pharmaceutical compositions are chosen carefully to prevent the side effects while maintaining the therapeutic efficacy of tesofensine.

The beta blocker may for example be selected from metoprolol, carvedilol or pharmaceutically acceptable salts thereof.

The second composition may be a first coating applied to the first composition.

The third composition may be a second coating applied to the first coating.

The first composition may be coated with a coating comprising the second and third composition.

The first composition may constitute a tablet core coated with a coating comprising the second and third composition. Alternatively, the first composition may comprise a tablet core coated with a first coating comprising the second composition, wherein the first layer is coated with a second coating comprising the second composition.

In some embodiments, the first composition comprises pellets comprising:
a. an inert pellet core;
b. a drug layer comprising the active pharmaceutical ingredient, which layer covers the inert core; and
c. a controlled release layer thereon.

The inert core may comprise sugar spheres coated with a plasticized film sub-coat of a hydrophobic film coating polymer plasticized with a hydrophilic and a hydrophobic plasticizer; the drug layer comprises API and a binder; the controlled release layer comprises a plasticized film coat of a hydrophobic film coating polymer plasticized with a hydrophilic and a hydrophobic plasticizer, and wherein the pellets are mixed with a final tableting blend e.g. comprising a powder mixture of one or more of fillers, disintegrants, glidants and/or lubricants.

In one embodiment, the hydrophobic film coating polymer comprises ethyl cellulose, the hydrophilic plasticizer comprises polyethylene glycol, the hydrophobic plasticizer comprises dibutyl sebacate, the API is metoprolol succinate, the binder comprises povidone, and the powder mixture comprises STARLAC (an excipient that is 85% of alpha-lactose monohydrate and 15% white maize starch) (MEGGLE Group, Germany), SYLOID (silica) (W.R. Grace & Co.), crospovidone and magnesium stearate.

In another embodiment, the extended release layer comprises an admixture of the following components:
a. an ethylacrylate/methylmethacrylate copolymer,
b. a surfactant, and
c. sodium stearyl fumarate,
wherein the controlled release layer has been deposited from a water-containing liquid and the amount of the ethylacrylate/methylmethacrylate copolymer in the film coat is in the range of 80-99.5% (w/w).

The composition may be in the form of a pharmaceutical dosage form, such as a tablet or a capsule. A tablet may comprise an outer cosmetic film coat.

In another aspect, the composition is for use in a method of treatment, prevention or alleviation of obesity or an obesity-related disorder.

In yet another aspect, the present invention relates to use of the composition as described herein in the manufacture of a medicament for the treatment of obesity or an obesity-related disorder.

The obesity associated disorder may be a disorder or condition selected from the group consisting of type 2 diabetes, pre-diabetes, type 1 diabetes (diabetes mellitus), metabolic syndrome, dyslipidemia, atherosclerosis, drug-induced obesity, overeating disorders, bulimia nervosa, binge eating disorder, compulsive over-eating, impaired appetite regulation, nonalcoholic fatty liver disease (NAFLD), and nonalcoholic steatohepatitis (NASH).

In one embodiment, the obesity-associated disorder or condition is type 2 diabetes.

In one embodiment, the obesity-associated disorder or condition is nonalcoholic fatty liver disease (NAFLD) and/or nonalcoholic steatohepatitis (NASH).

In another aspect, the composition is for use in a method of treatment, prevention or alleviation of diabetes, preferably type 2 diabetes.

In another aspect, the composition is for use in a method of treatment, prevention or alleviation of nonalcoholic fatty liver disease (NAFLD) and/or nonalcoholic steatohepatitis (NASH).

In another aspect, the composition is for use in a method of decreasing liver fat and/or visceral adiposity.

Preferably the composition is administered once daily.

DEFINITIONS

Figure 1A:
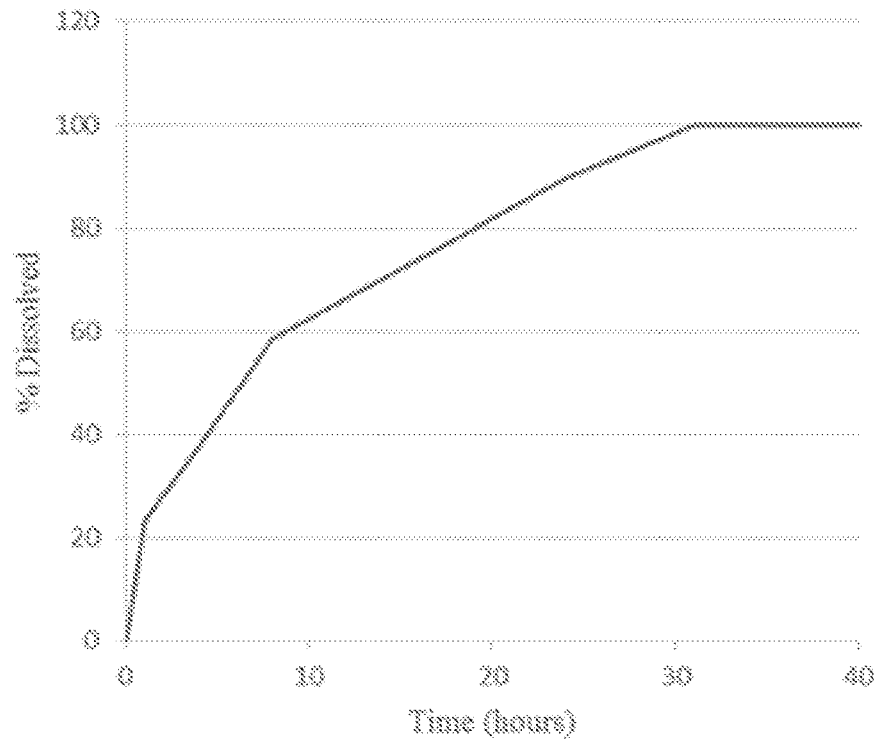
FIG. 1A: Calculated dissolution profile for tablet with 25 mg IR metoprolol and 100 mg ER metoprolol. Calculated dissolution profile of metoprolol over 24 hours using USP Type II apparatus, rotating paddle, with 900 ml of Phosphate buffer at pH 7.4, 37° C. set at rotating speed of 75 rpm.

Extended release—ER—also known as sustained-release [SR], extended-release [ER, XR, XL], and controlled-release [CR], is a mechanism used in pill tablets or capsules to dissolve a drug over time in order to be released slower and steadier into the bloodstream.

Immediate release—IR. The drug is released (dissolved) immediately after ingestion.

DETAILED DESCRIPTION OF THE INVENTION

Disclosed herein are pharmaceutical compositions comprising two different phases of a beta blocker, and one phase of tesofensine. One phase of the beta blocker is an extended release phase and the other phase is an immediate release phase.

The beta blocker may for example be metoprolol or carvedilol or pharmaceutically acceptable salts thereof. These include the phosphate, succinate, maleate, sulfate, glutarate, lactate, benzoate, and mandelate salts.

The in vitro bio-dissolution profile (as determined by USP Type II apparatus, rotating paddle, with 500 ml of Phosphate buffer at pH 7.4, 37° C. set at rotating speed of 50 rpm) of the beta blocker is preferably as follows:

| Dissolution time | Range |
| --- | --- |
| 1 hour | 10-35% |
| 4 hours | 25-45% |
| 8 hours | 45-65% |
| 20 hours | >80% |

For example, the combined in vitro bio-dissolution profile of metoprolol preferably has a dissolution profile lying within one or more of the following release ranges for different metoprolol IR:ER ratios at various time points (as determined by USP Type II apparatus, rotating paddle, with 900 ml of Phosphate buffer at pH 7.4, 37° C. set at rotating speed of 75 rpm).

| Dissolution time | Calculated dissolution 10 mg IR + 100 mg ER | Dissolution ranges (10:100) | Calculated dissolution 25 mg IR + 100 mg ER | Dissolution ranges (25:100) | Overall range |
| --- | --- | --- | --- | --- | --- |
| 1 hour | 13% | 10-20% | 23% | 20-30% | 10-30% |
| 4 hours | 29% | 20-40% | 38% | 30-50% | 20-50% |
| 8 hours | 53% | 40-65% | 58% | 50-70% | 40-70% |
| 24 hours | 88% | >80% | 90% | >80% | >80% |

| Dissolution time | Calculated dissolution 10 mg IR + 100 mg ER | Dissolution ranges (10:100) | Calculated dissolution 25 mg IR + 100 mg ER | Dissolution ranges (25:100) | Overall range |
| --- | --- | --- | --- | --- | --- |
| 1 hour | 13% | 10-20% | 23% | 20-30% | 10-30% |
| 4 hours | 29% | 20-40% | 38% | 25-50% | 20-50% |
| 8 hours | 53% | 40-65% | 58% | 40-70% | 40-70% |
| 20 hours | 88% | >80% | 90% | >80% | >80% |

In general the tesofensine of the composition is dissolved within ½-1 hour. The in vitro dissolution profile with tesofensine under the conditions above is at least 80% of the API within 45 minutes.

Many physiological factors influence both the gastrointestinal transit time and the release of a drug from a controlled release dosage form, and thus influence the uptake of the drug into the systemic circulation. A sustained-release dosage form should release the beta blocker at a controlled rate such that the amount of active ingredient available in the body to treat the condition is maintained at a relatively constant level over an extended period of time. The release of an active ingredient from a controlled release dosage form is generally controlled by diffusion through a coating.

It is likewise important that part of the beta blocker is released rapidly so that a therapeutically effective level of the beta blocker is reached rapidly.

Tesofensine

The pharmaceutical composition described herein comprises an active pharmaceutical ingredient (API) selected from tesofensine or a pharmaceutically acceptable salt thereof.

Tesofensine [(1R,2R,3S,5S)-3-(3,4-dichlorophenyl)-2-(ethoxymethyl)-8-methyl-8-azabicyclo[3.2.1]octane] is a centrally acting triple monoamine re-uptake inhibitor (MRI) with intrinsic inhibitory activity on noradrenaline, serotonin and dopamine transporter function. When corrected for placebo and diet effects, long-term Tesofensine treatment produces a weight loss of about 10% in obese patients, which is twice as much as that achieved by currently marketed anti-obesity drugs.

The chemical structure of Tesofensine is

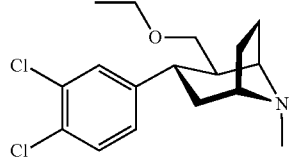

Preclinical and clinical data suggest that appetite suppression is an important mechanism by which Tesofensine exerts its robust weight-reducing effect. In addition, Tesofensine has also been demonstrated to increase nocturnal energy expenditure in human subjects. These findings have recently been corroborated and extended in preclinical settings, demonstrating that Tesofensine induces a robust and sustained weight loss in a rat model of diet-induced obesity (DIO) of which the long-lasting reduction in body weight is caused by appetite suppression with a gradual increase in energy expenditure. Notably, the hypophagic effect of Tesofensine in DIO rats is critically dependent on stimulated $\alpha 1$ adrenoceptor activity, and to a less extend dopamine D1 receptor function, indicating that enhancement of central noradrenergic and dopaminergic neurotransmission constitute important mechanisms underlying the robust appetite-suppressing effect of Tesofensine.

Overall, chronic Tesofensine treatment is associated with minor adverse events, and with minimal cardiovascular effects, suggesting that Tesofensine may generally be a well-tolerated long-term treatment for obesity. However, dose-dependent elevations in heart rate and significant increases in blood pressure have been reported in obese individuals. The long-term implications of such Tesofensine-induced cardiovascular effects are not known and can potentially play a role in the benefit/risk evaluation of patients treated with Tesofensine.

Beta Blockers

The present invention involves the use of beta blockers. The beta blocker may be any conventional beta blocker known in the art. Preferably, the beta blocking drug is selected from the following groups of compounds, which groups of compounds are known in the art and may be commercially available under different brand names, or may be obtained as described in the literature.

Non-Selective Beta Blockers

In one embodiment, the beta blocker is a non-selective beta blocker. Examples of non-selective beta blockers include alprenolol, amosulalol, bucindolol, carteolol, levobunolol, mepindolol, metipranolol, nadolol, oxprenolol, penbutolol, pindolol, propranolol, sotalol and timolol.

In one embodiment, the beta blocker is selected from the group consisting of alprenolol, amosulalol, bucindolol, carteolol, levobunolol, mepindolol, metipranolol, nadolol, oxprenolol, penbutolol, pindolol, propranolol, sotalol, timolol and pharmaceutically acceptable salts thereof.

Beta 1-Selective Beta Blockers

In another embodiment, the beta blocker is a beta 1-selective beta blocker.

Examples of beta 1-selective beta blockers include acebutolol, atenolol, betaxolol, bisoprolol, esmolol, landiolol, metoprolol and nebivolol.

In one embodiment, the beta blocker is selected from the group consisting of acebutolol, atenolol, betaxolol, bisoprolol, esmolol, landiolol, metoprolol, nebivolol and pharmaceutically acceptable salts thereof.

In a particular embodiment, the beta blocker is metoprolol or a pharmaceutically acceptable salt thereof.

Mixed Alpha and Beta Blockers

In a still further embodiment, the beta blocker is a mixed alpha and beta blocker.

Examples of mixed alpha and beta blockers include carvedilol, celiprolol and labetalol.

In one embodiment, the beta blocker is selected from the group consisting of carvedilol, celiprolol, labetalol and pharmaceutically acceptable salts thereof.

In a particular embodiment, the beta blocker is carvedilol or a pharmaceutically acceptable salt thereof.

Beta 2-Selective Beta Blockers

In a still further embodiment, the beta blocker is a beta 2-selective beta blocker.

One example of a beta 2-selective beta blocker is butaxamine.

In one embodiment, the beta blocker is butaxamine or a pharmaceutically acceptable salt thereof.

Pharmaceutically Acceptable Salts

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of an API include, without limitation, the sodium, the potassium, the calcium, the magnesium, the zinc, the aluminium, the lithium, the choline, the lysinium, and the ammonium salt, and the like, of an API containing an anionic group. Such cationic salts may be formed by procedures well known and described in the art.

In the context of this disclosure the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

In one embodiment of the present disclosure, Tesofensine is selected from the free base, the citrate salt and the tartrate salt.

Suitable pharmaceutically acceptable salts of metoprolol include any of the salts mentioned herein and preferably include the tartrate, succinate, fumarate or benzoate salts and especially the succinate salt. The S-enantiomer of metoprolol or a salt thereof, particularly the benzoate salt or the sorbate salt, may also be used.

Similarity Factors

Similarity factor (f2) is a recognized method for the determination of the similarity between the dissolution profiles of a reference and a test compound. Similarity factor (f2) is a logarithmic transformation of the sum of squared error. The similarity factor (f2) is 100 when the test and reference profiles are identical and approaches zero as the dissimilarity increases. The similarity factor has also been adapted to apply to the determination of the similarity between the dissolution profiles of a reference and test compound as they relate to modified release formulations, such as those exemplified herein.

The f2 similarity factor has been adopted in the SUPAC guidelines and by the FDA guidance on dissolution testing of immediate release dosage forms (FDA Guidance for Industry, Dissolution Testing of Immediate Release Solid Oral Dosage Forms, FDA, (CDER), August 1997 (Dissolution Tech. 4, 15-22, 1997)).

Figure 1B:
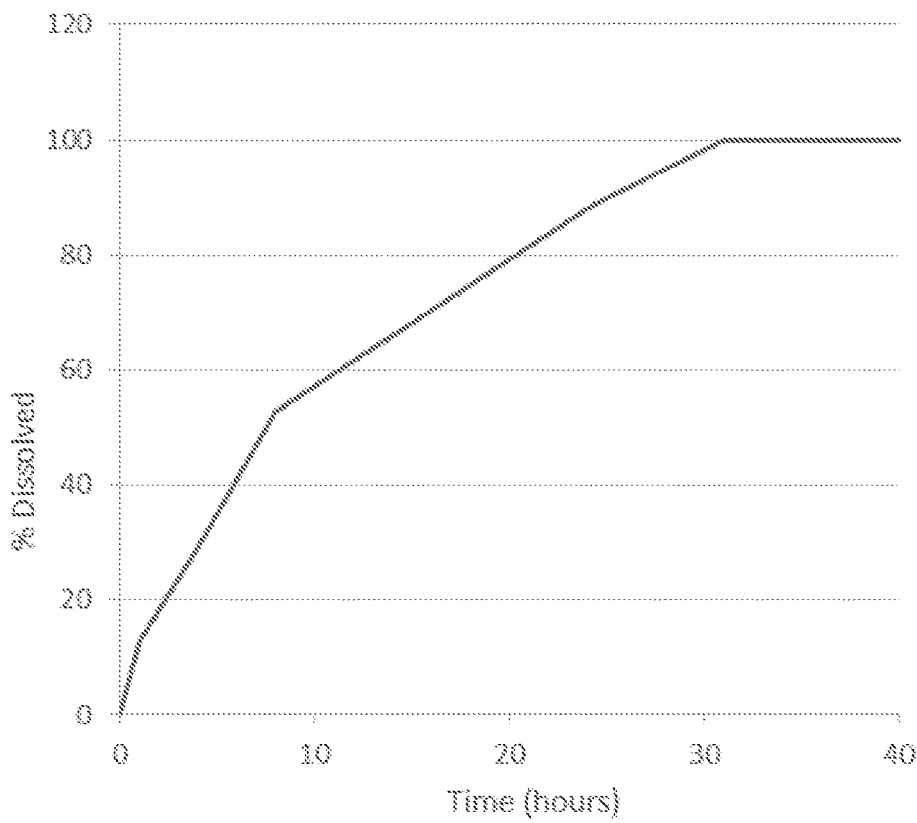
FIG. 1B: Calculated dissolution profile for tablet with 10 mg IR metoprolol and 100 mg ER metoprolol. Calculated dissolution profile of metoprolol over 24 hours using USP Type II apparatus, rotating paddle, with 900 ml of Phosphate buffer at pH 7.4, 37° C. set at rotating speed of 75 rpm.
Figure 2A:
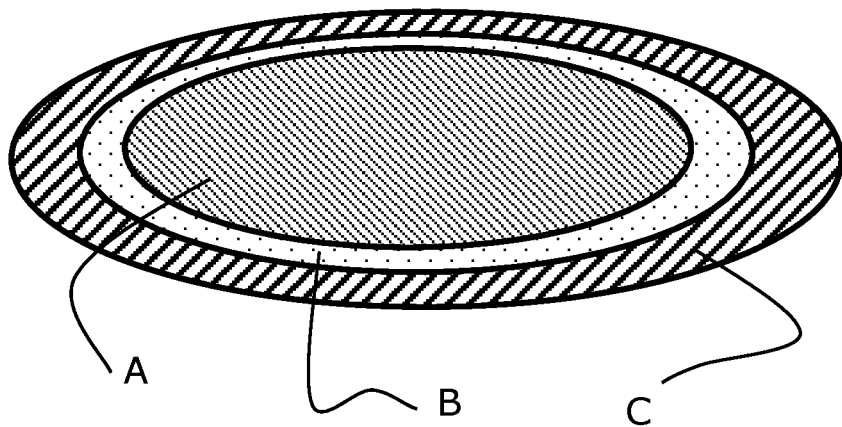
FIG. 2A: Schematic cross-sections of tablet with beta blocker ER (A), beta blocker IR (B) and Tesofensine (C) phases. A three layered tablet with a core of beta blocker ER and two coatings of beta blocker IR and Tesofensine.
Figure 2B:
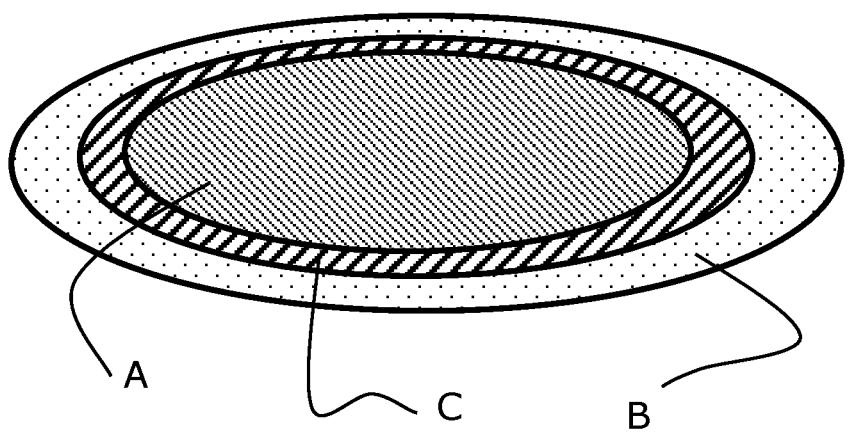
FIG. 2B: Schematic cross-sections of tablet with beta blocker ER (A), beta blocker IR (B) and Tesofensine (C) phases. As in 2A but with the order of the coatings reversed.
Figure 2C:
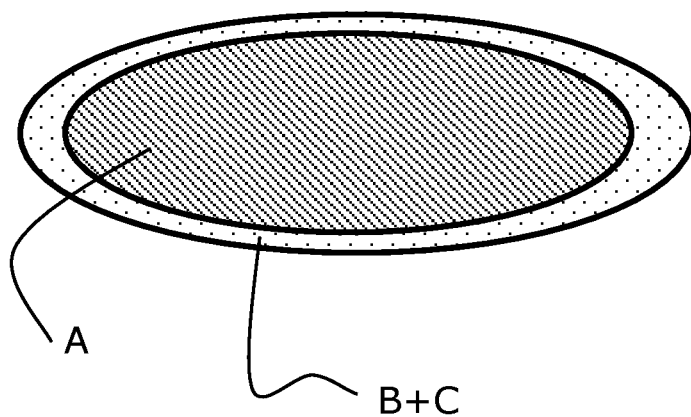
FIG. 2C: Schematic cross-sections of tablet with beta blocker ER (A), beta blocker IR (B) and Tesofensine (C) phases. A two layered tablet with a core of beta blocker ER and one coating of beta blocker IR and Tesofensine.
Figure 2D:
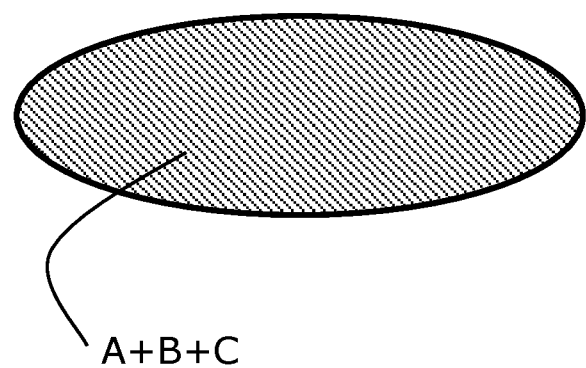
FIG. 2D: Schematic cross-sections of tablet with beta blocker ER (A), beta blocker IR (B) and Tesofensine (C) phases. A one layered tablet with beta blocker ER spheres/granules in a binding matrix comprising beta blocker IR and Tesofensine.
Figure 3:
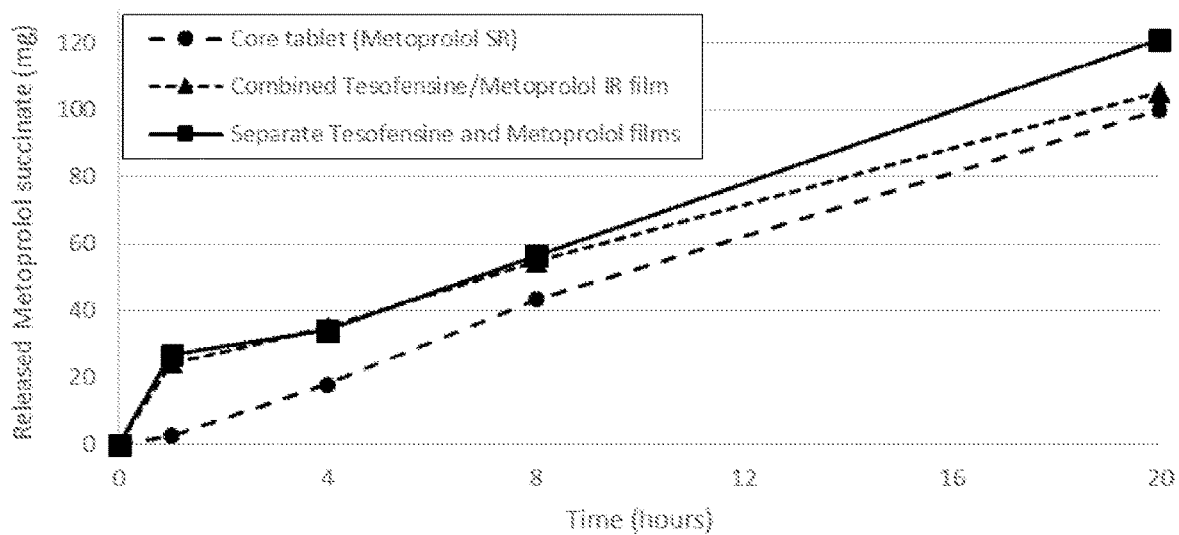
FIG. 3: Release of Metoprolol from Metoprolol 100 mg ER tablets with combined Tesofensine/Metoprolol film applied (example 7) and Metoprolol 100 mg ER tablets with separate Tesofensine—and Metoprolol IR films applied (Example 6).

Preferably the pharmaceutical composition has a beta blocker in vitro dissolution profile generated using the USP Type II apparatus, rotating paddle method as described herein with a similarity factor (f2) between 50 and 100 when calculated using one of the examples from FIG. 1 or FIG. 3 as the reference profile.

API Amounts and Ratios

The ratio of extended release beta blocker, such as metoprolol, to immediate release beta blocker may be 75-95:25-5. Suitably, the beta blocker, such as metoprolol, in a dosage form is approximately an 80:20 ratio of extended release to immediate release amounts. In another embodiment, the beta blocker, such as metoprolol, is in an approximate 90:10 or 100:10 ratio of extended to immediate release amounts. In still another embodiment the ratio is approximately 80:20 or 75:25. Explained differently, for unit dosage form, such as a tablet, containing 125 mg beta blocker, such as metoprolol, the beta blocker may be present in an amount of about 100 mg in the extended release phase and about 25 mg in the immediate release phase. For a unit dosage form comprising 110 mg beta blocker, such as metoprolol, the beta blocker ER may be present in an amount of 100 mg and the beta blocker IR may be present in an amount of 10 mg. For example, in one embodiment, the ratios of extended release to immediate release phase represent the proportional amount of each layer in a bi-layer dosage form. In another embodiment, the ratios represent the amount of metoprolol in the extended release intragranular component versus the immediate release extragranular component of a single layer dosage form. The rations and amounts mentioned in the current paragraph apply well to metoprolol as the beta-blocker.

Preferably one dosage form comprises an amount of beta blocker, such as metoprolol, ER of 25-200 mg API, such as 50-200 mg of API, preferably 50-150, such as 75-125, for example about 80 mg or about 100 mg.

Other beta-blockers, such as carvedilol may require lower dosages. In this case one dosage form may comprise an amount of beta blocker, such as carvedilol, ER of 20-100 mg of API, preferably 30-80, for example about 20 mg, 40 mg or about 80 mg.

The amount of tesofensine per dosage form (in the second composition) is generally from 0.1-1 mg API, preferably 0.2-0.8 mg, for example 0.25-0.75 mg, such as 0.4-0.6 mg for example about 0.25 mg, 0.5 mg or 0.75 mg.

The amount of beta blocker, such as metoprolol, IR per dosage form may be from 5-100 mg API, for example 50-80 mg, preferably 10-75 mg, such as 10-50 mg, such as 20-30 mg or 10-20 mg, for example about 5 mg, about 10 mg, about 15 mg, or about 25 mg.

Thus one dosage form may comprise 50-200 mg ER beta blocker, such as metoprolol, 5-50 mg IR beta blocker, such as metoprolol, and 0.1-1.5 mg tesofensine; for example 75-125 mg ER beta blocker, such as metoprolol, 10-25 mg IR beta blocker, such as metoprolol, and 0.25-0.75 mg tesofensine; for example 75-80 mg ER beta blocker, such as metoprolol, 10-15 mg IR beta blocker, such as metoprolol, and 0.25-0.75 tesofensine; for example 75-85 mg ER beta blocker, such as metoprolol, 15-25 mg IR beta blocker, such as metoprolol, and 0.25-0.75 tesofensine; for example 90-110 mg ER beta blocker, such as metoprolol, 20-30 mg IR beta blocker, such as metoprolol, and 0.25-0.75 tesofensine.

Thus one dosage form may comprise 20-100 mg ER beta blocker, such as carvedilol, 5-40 mg IR beta blocker, such as carvedilol, and 0.1-1.5 mg tesofensine; for example 30-80 mg ER beta blocker, such as carvedilol, 5-20 mg IR beta blocker, such as carvedilol, and 0.25-0.75 mg tesofensine; for example 40-80 mg ER beta blocker, such as carvedilol, 10-20 mg IR beta blocker, such as carvedilol, and 0.25-0.75 tesofensine.

In one embodiment the beta blocker is metoprolol and the amount of the two APIs in the three phases of the current dosage form are present in the following absolute amounts.

| Metoprolol ER | Metoprolol IR | Tesofensine IR |
|---|---|---|
| 50-200 mg | 5-50 mg | 0.1-1.5 mg |
| 75-125 mg | 10-25 mg | 0.25-0.75 mg |
| 75-80 mg | 10-15 mg | 0.25-0.75 mg |
| 100 mg | 25 mg | 0.5 mg |
| 100 mg | 10 mg | 0.5 mg |
| 80 mg | 20 mg | 0.5 mg |

In one embodiment the beta blocker is carvedilol and the amount of the two APIs in the three phases of the current dosage form are present in the following absolute amounts.

| Carvedilol ER | Carvedilol IR | Tesofensine IR |
|---|---|---|
| 20-100 mg | 5-25 mg | 0.1-1.5 mg |
| 30-80 mg | 5-20 mg | 0.25-0.75 mg |
| 80 mg | 20 mg | 0.25-0.75 mg |
| 40 mg | 10 mg | 0.5 mg |
| 20 mg | 5 mg | 0.5 mg |

Multi-Layer Dosage Form

The extended release phase may be part of a multiple layer tablet, such as a bi or tri-layer dosage form.

In one embodiment, the dosage form comprises a tri-layer dosage unit having an extended release (ER) phase layer with a beta blocker, such as metoprolol or carvedilol, and one immediate release phase layer with a beta blocker, such as metoprolol or carvedilol and another immediate release layer with tesofensine. The ER phase contains a therapeutically effective amount of the beta blocker, such as metoprolol or carvedilol, suitably in granulate form.

In other embodiments, the dosage form is a bi-layer tablet having an ER phase layer with a beta blocker, such as metoprolol or carvedilol and one immediate release layer with both the beta blocker (such as metoprolol or carvedilol) and tesofensine.

Extended Release Phase

Extended release compositions of beta blockers, such as metoprolol or pharmaceutically acceptable salts of metoprolol are known the art. Non-limiting examples of disclosures of such compositions are found in: WO 2015/004617, WO 2013/084089, WO 2013/030725, WO 2012/052834, WO 2011/143420, WO 2007/09770, WO 2004/069234, WO 2007/110753, WO 2007/029070, WO 2008/012346, and WO 2007/048233. Such extended release compositions typically involve coating the API with an extended release layer that provides an approximated zero-order rate of dissolution of the API.

In one embodiment, the extended release beta blocker, such as metoprolol, is formulated as pellets with pharmaceutically acceptable excipients such as for example binders, film coating polymers, plasticizers, starch, glidants, and disintegrants.

An extended release formulation of carvedilol is also known from U.S. Pat. No. 8,101,209 (Flamel Technologies).

Inert Core

In some embodiments, the pellets comprise an initial core (inert core) coated with a layer of a beta blocker, such as metoprolol or a metoprolol salt, and further coated with an extended release layer.

As used herein the term initial core refers to a pharmaceutically acceptable core for use in pharmaceutical formulations which core is inert.

In one embodiment there is provided a pharmaceutical composition for extended release comprising pellets coated with a beta blocker, such as metoprolol or a metoprolol salt, wherein each coated pellet comprises a) an inert core comprising at least 50% (w/w) of soluble substance; b) a drug layer comprising the beta blocker, such as metoprolol, which layer covers the inert core; and c) a controlled release layer thereon.

In another embodiment there is provided a pharmaceutical composition wherein the release rate of drug from the pellets part of the pharmaceutical composition comprising a tableted or encapsulated composition of a multitude of pellets is controlled by the amount or the percentage of the initial core/spheres of the pellets. Preferably, the amount of initial core is from about 15% to about 35% by weight of the controlled release coated pellets before tableting or capsule filling, such as from 20-30%.

In another embodiment the inert core is strengthened by applying a sub-coat on the initial core/sphere. In pharmaceutical compositions wherein pellets comprising the drug are compressed into tablets, the drug pellets are mixed with powder excipients to form a tableting blend. However, the size of the drug coated pellets, often larger than the particle size of the powder excipients, can cause a lack of uniformity of the tableting blend. The preferred uniformity of the tableting blend is such that the average assay of samples of the tableting blend each weighing the equivalent of one tablet lies within the range of 90 to 110 percent of the label dose and the relative standard deviation of the individual assays is less than or equal to 5 percent. The size of the drug pellets is therefore preferably small. When layering a large amount of drug on a small initial core a high degree of stress is exerted on the initial core. This stress may cause attrition particularly when the inert core comprises sugar spheres. To provide a higher degree of physical strength of the inert core without changing the dissolution rate of drug coated pellets, a sub-coat may be applied on an initial core/sphere. Preferably, the amount of the sub-coat is from about 10% to about 40% of the total weight of the sub-coated inert core, more preferably the amount of sub-coat is from about 15% to about 30% of the total weight of the sub-coated inert core, most preferably the amount of sub-coat is about 16% to about 20% of the total weight of the sub-coated inert core.

The inert core of each of the pellets in the pharmaceutical composition may comprise from about 50% to about 100% (per weight) of soluble substance. Preferably the inert core comprises from about 70% to about 90% (per weight) of soluble substances. A preferred initial core comprises a sugar sphere. Sugar spheres have been used in the pharmaceutical industry as excipients. Such sugar spheres used in pharmaceutical compositions generally contain not more than 92% of sucrose, calculated on the dried basis, the remainder consisting of maize starch. Commonly sugar spheres with a core size larger than 500 μm are used. The core size of the inert cores, preferably a sugar sphere, is between about 50 μm and about 500 μm, preferably between about 100 μm and about 400 μm, more preferably from about 250 μm to about 350 μm.

The inert core may comprise an initial core/sphere that is sub-coated with a layer of a plasticized film coating polymer. This sub-coating of an initial core/sphere provides physical strength to the inert core. The film coating polymer may be a hydrophobic or a hydrophilic polymer, or a combination of the two. Suitable film coating polymers can be cellulose derivative polymers or polymethacrylate polymers. Further, hydrophobic polymers or hydrophilic plasticizers, or a combination of several plasticizers can be used to plasticize the film coating polymers. These compounds of the polymeric sub-coat are mixed with solvents prior to their application onto the initial core/sphere. Suitable solvents for use in mixing the polymeric sub-coating compounds are selected from ethanol, isopropyl alcohol, acetone and purified water. For example a mixture of ethanol, acetone and water is preferred for use in mixing a mixture of the preferred sub-coating compounds EthylCellulose (as a film coating polymer), and plasticizers Dibyutyl Sebacate and Polyethylene Glycol (EC, DBS and PEG).

Preferably, the initial core/sphere is a sugar sphere which is sub coated with a mixture of polymers such as cellulose derivatives e.g. ethylcellulose and triethyl citrate, polyethylene glycol, dibutyl sebacate, and dibutyl phthalate, and wherein the sub-coating layer on the initial core/sphere does not alter the release rate of the drug for the pharmaceutical composition. A preferred sub-coat on the sugar spheres comprises ethyl cellulose as a hydrophobic film coating polymer and a combination of two or more plasticizers, at least one hydrophilic and at least one hydrophobic plasticizer. Suitable plasticizers may include for example polyethylene glycols, citrate esters, dibutyl sebacate, diethyl phthalate, and triacetin. Preferred plasticizers are polyethylene glycol and dibutyl sebacate as the hydrophilic and hydrophobic plasticizers respectively. Preferably, the sub-coat comprises about 75% to about 85% ethyl cellulose, about 10% to about 20% polyethylene glycol and about 3% to about 7% dibutyl sebacate by weight of the sub-coat. More preferably, the sub-coat comprises 80% ethyl cellulose, 15% polyethylene glycol and 5% dibutyl sebacate by weight of the sub-coat.

Alternatively the core may be an insoluble core onto which the active ingredient has been deposited for example by spraying. It may be made from silicon dioxide, glass or plastic resin particles. Suitable types of plastic material are pharmaceutically acceptable plastics such as polypropylene or polyethylene preferably polypropylene. Such insoluble cores may have a diameter in the range of 0.01-2 mm, preferably in the range of 0.05-1.0 mm and more preferably in the range of 0.1-0.7 mm.

Beta Blockers for Extended Release

In one embodiment, a beta blocker, such as Metoprolol or its acceptable pharmaceutical salt, may be applied on the inert core. No use of "Class 2" solvents (as defined by the FDA) is required to apply the active pharmaceutical ingredient (API), drug, onto the inert core forming a drug coated pellet. The FDA defines "Class 2" solvents as having inherent toxicity. The active ingredient is dispersed in water, preferably together with an acceptable binder excipient such as, but not limited to, polyvinyl pyrrolidone, cellulose derivatives polymers, or starch.

The beta blocker, such as metoprolol may be applied as a dispersion rather than a solution. Therefore it is preferred that the drug substance has physical properties that will allow a high yield in preparing drug coated pellets. Therefore, the drug substance preferably has a particle size distribution such that the d(0.9) value is less than about 80 μm. Preferably, the d(0.9) value for the particle size distribution of the drug substance is less than about 50 μm, more preferably less than about 30 μm. As a result, a concentrated dispersion for application can be produced which may shorten the production time.

The drug coated pellets may comprise from about 40% to about 90% (per weight) of the drug layer, preferably from about 50% to about 80% (per weight), more preferably from about 55% to about 75% (per weight).

Other beta blockers, such as Carvedilol or salts thereof, may be applied in a similar as indicated for Metoprolol.

Controlled Release Layer

The last layer applied on the pellets is a layer which controls the release of the active pharmaceutical ingredient. Pellets that have been coated with a controlled release layer may have a size between about 200 μm and about 800 μm. Preferably, the controlled release layer coated pellets have a size ranging from about 300 μm to about 700 μm, more preferably from about 400 μm to about 600 μm. In addition, the controlled release layer may comprise water soluble and insoluble components. Such components may be film forming polymers and plasticizers. For example, a film comprising a polymeric layer may be applied onto the drug coated pellets.

In the following three different types of extended release coatings are described.

First Extended Release Coating.

In one embodiment the extended release film coat comprises i) an acrylic polymer ii) a surfactant and iii) sodium stearyl fumarate, wherein the film coat has been deposited from a water containing liquid.

Typically a film coating composition comprises
a) 25 to 35% by weight of an acrylic polymer dispersion
b) 0.1 to 4% by weight of a surfactant
c) 0.1 to 4% sodium stearyl fumarate and
d) a water-containing liquid to 100%.

In one embodiment there is provided film coatings which are suitable for giving extended release. Suitably the acrylic polymer used in this case comprises homogeneous particles wherein the polymer or copolymer has $T_g$<room temperature in aqueous dispersion but has $T_g$>room temperature in the dry state. Suitable polymers comprise acrylic acid and esters thereof particularly the methyl, ethyl, propyl and butyl esters; and methacrylic acid and esters thereof particularly the methyl, ethyl, propyl and butyl esters. Particularly preferred polymers are those provided under the tradenames Eudragit L30D® (Rohm Pharma) or Eudragit FS30D® (Rohm Pharma). Optionally further anti-tacking agents may be required.

Suitably the amount of the acrylic polymer in the film coating composition is in the range of 15 to 50% by weight. Preferably the amount of the acrylic polymer in the film coating composition is in the range of 20 to 40% by weight. More preferably the amount of the acrylic polymer in the film coating composition is in the range of 25 to 35% by weight.

Suitably the surfactant is one of the following: a nonionic surfactant, like sorbitan esters (Span series); polysorbates (Tween series); polyoxyethylated glycol monoethers (like the Brij series); polyoxyethylated alkyl phenols (like the Triton series or the Igepal series); alkyl glucosides (e g dodecylmaltoside); sugar fatty acid esters (e g sucrose laurate); saponins; etc: or mixtures thereof; ampholytic surfactants, like betaines; anionic surfactants, like sulphated fatty alcohols eg sodium dodecylsulphate SDS; sulphated polyoxyethylated alcohols; others like dioctyl sulphosuccinate; bile salts (e g dihydroxy bile salts like sodium deoxycholate, trihydroxy bile salts like sodium glycocholate, etc); fusidates (e g sodium dihydrofusidate); etc cationic surfactants, like ammonium compounds; soaps, fatty acids, and lipids and their salts, like alkanoic acids; (e g octanoic acid, oleic acid); monoglycerides (eg monolein), phospholipids which are neutral or positively or negatively charged (eg dialkyl phosphatidylcholine, dialkyl phosphatidylserine, etc); etc; more preferably the surfactant is a nonionic surfactant. Most preferably the surfactant is nonoxynol 100.

Suitably the amount of the surfactant in the film coating composition is in the range of 0.05 to 8% by weight. Preferably the amount of the surfactant in the film coating composition is in the range of 0.1 to 6% by weight. More preferably the amount of the surfactant in the film coating composition is in the range of 0.5 to 4% by weight.

In a most preferred embodiment the acrylic polymer and the surfactant are provided by Eudragit® NE30D in compositions, a film coats or formulations defined previously.

Suitably the amount of the sodium stearyl fumarate in the film coating composition is in the range of 0.05 to 8% by weight. Preferably the amount of sodium stearyl fumarate in the film coating composition is in the range of 0.1 to 6% by weight. More preferably the amount of sodium stearyl fumarate in the film coating composition is in the range of 0.5 to 4% by weight.

Suitably the water-containing liquid comprises water and a water miscible organic liquid for example lower alkanols e.g. ethanol, propanol or isopropanol. From a safety point of view is preferred that the proportion of the organic is kept to a minimum but small amounts are tolerable for example in the range of 0 to 20% by volume. Preferably the liquid is water.

The film-coating composition is particularly suitable for use as an aqueous film-coating composition wherein the film-coat is applied using water as the liquid. When the liquid is water the latex is preferably a poly(ethylacrylate-co-methylmethacrylate) copolymer, for example Eudragit NE30D® (Rohm Pharma). This process is particularly advantageous as it negates the need to use environmentally unacceptable organic solvents, some of which also present processing problems due to their inflammability, while also eliminating many of the problems experienced with aqueous coatings described above.

Second Extended Release Coating

Alternatively, the film may comprise at least one film coating polymer and can be plasticized with one or more plasticizers. These plasticizers may differ from each other in their degree of solubility (hydrophobicity/hydrophilicity). By changing the ratio between the plasticizers and the film coating polymer, or the ratio between the different plasticizers (if more than one is used), one can control the rate of the release of the drug from the pellets. The controlled release layer of the beta blocker ER may comprise a hydrophobic film coating polymer such as for example ethylcellulose and a combination of at least two plasticizers, at least one hydrophilic and one hydrophobic plasticizer, for example polyethylene glycol and dibutyl sebacate. Preferably, the ratio of hydrophobic to hydrophilic plasticizer in the controlled release layer of the pharmaceutical composition is from 3:1 to 1:3, more preferably the ratio is 1:1.

Furthermore, the controlled release layer may comprise at least about 70% water insoluble compounds (per weight of the controlled release layer). Preferably, the controlled release layer comprises at least about 80% and more preferably at least about 90% water insoluble compounds (per weight of the controlled release layer). Suitable water insoluble compounds are for example cellulose derived polymers. These controlled release layer compounds are mixed with solvents prior to their application onto the drug coated pellets. Suitable solvents for use in mixing the controlled release layer compounds are selected from ethanol, isopropyl alcohol, acetone and purified water. A mixture of ethanol, acetone and water is preferred for use in mixing the controlled release layer compounds especially where the controlled release layer compounds are a mixture of ethylcellulose, dibutyl sebacate and polyethylene glycol.

The method of preparing the beta blocker ER component may comprise sub-coating an initial core/sphere forming an inert core. Sub-coating an initial core/sphere comprises mixing a film coating polymer with one or more plasticizers in a solvent forming a coating mixture. Such mixture may be a solution, suspension or slurry for applying a coating layer on a surface. The coating mixture is applied to the initial core/sphere forming a sub-coated initial core/sphere which is used as an inert core. The film coating polymer may be a hydrophobic or a hydrophilic polymer, or a combination of the two. Suitable film coating polymers can be cellulose derivative polymers or polymethacrylate polymers, preferably ethylcellulose. The amount of ethylcellulose is preferably from about 75% to about 85% more preferably about 80% of the total amount of the weight of the sub-coat. Further, hydrophobic polymers or hydrophilic plasticizers, or a combination of several plasticizers can be used to plasticize the film coating polymers. These compounds of the polymeric sub-coat are mixed with solvents prior to their application onto the initial core/sphere. Suitable solvents for use in mixing the polymeric sub-coating compounds are selected from ethanol, isopropyl alcohol, acetone and purified water. A mixture of ethanol, acetone and water is preferred for use in mixing the polymeric sub-coating compounds.

Suitable plasticizers for use in sub-coating an initial core/sphere are selected from polyethylene glycol, dibutyl sebacate, and dibutyl phthalate. Preferred plasticizers are polyethylene glycol and dibutyl sebacate as the hydrophilic and hydrophobic plasticizers respectively. Preferred amounts of plasticizers used in the method are about 10% to about 20% polyethylene glycol and 3% to about 7% dibutyl sebacate by weight of the sub-coat. More preferably, about 15% polyethylene glycol and 5% dibutyl sebacate as plasticizer.

For the extended release coat, the amount of ethylcellulose is preferably from about 75% to about 85% more preferably about 80% of the total amount of the weight of the coat. Suitable plasticizers for use in the ER-coating are selected from polyethylene glycol, dibutyl sebacate, and dibutyl phthalate. Preferred plasticizers are polyethylene glycol and dibutyl sebacate as the hydrophilic and hydrophobic plasticizers respectively. Preferred amounts of plasticizers used in the method are about 5% to about 20% polyethylene glycol and dibutyl sebacate by weight of the ER-coat. More preferably, about 10% polyethylene glycol and 10% dibutyl sebacate as plasticizer.

In one embodiment, a metoprolol ER tablet comprises:

| Material | Weight | Percent total pellet weight |
|---|---|---|
| Sub-coated pellets | | |
| Sugar spheres (250-355 μm) | 598.00 | 22.3 |
| Ethyl cellulose 7 cps | 92.00 | 3.4 |
| Polyethylene glycol 400 | 17.25 | 0.6 |
| Dibutyl sebacate | 5.75 | 0.2 |
| Drug layer | | |
| Metoprolol succinate | 1092.50 | 40.9 |
| Polyvinyl pyrrolidone povidone (PVP K-30) | 276 | 10.3 |
| Controlled release film layer | | |
| Ethyl cellulose 100 cps | 473.8 | 17.7 |
| Polyethylene glycol 400 | 59.23 | 2.2 |
| Dibutyl sebacate | 59.23 | 2.2 |

In a preferred method of preparing the beta blocker ER part of the composition, the method comprises the following steps; a) providing sugar spheres as initial cores; b) coating the sugar spheres with a sub-coat comprising mixing a film of a hydrophobic polymer, a soluble (hydrophilic) plasticizer, and an insoluble (hydrophobic) plasticizer with a solvent mixture of e.g. acetone, ethanol 95%, and water and spraying the mixture onto the sugar spheres to create a sub-coat on the sugar spheres resulting in an inert core; c) coating the sub-coated sugar spheres (inert cores) with a drug layer comprising mixing the drug, such as metoprolol succinate, and a binder, preferably povidone (PVP K-30) with preferably water, forming an aqueous dispersion and applying the dispersion onto the sub-coated pellets (inert cores) forming drug coated pellets; d) applying a third layer on the drug coated pellets comprising dissolving a hydrophobic film coating polymer, an hydrophilic plasticizer and an hydrophobic plasticizer in a solvent mixture of e.g. acetone, ethanol 95%, and water forming a mixture and spraying the mixture onto the drug coated pellets to create controlled release drug coated pellets; e) mixing the controlled release drug coated pellets with a powder mixture of one or more excipients forming a final blend; f) compressing the final blend into tablets or filling the final blend into capsules; and g) optionally film coating the tablets for cosmetic purposes.

In this method the hydrophobic polymer is preferably ethyl cellulose (EC), the soluble/hydrophilic plasticizer is preferably polyethylene glycol (PEG), and the insoluble/hydrophobic plasticizer is preferably dibutyl sebacate (DBS). Further, in preparing a mixture for coating the sugar spheres with a sub-coat, and the drug coated pellets with a controlled release layer, ethyl cellulose is preferably first dissolved in acetone and ethanol 95%, then PEG and DBS are added, followed by adding water and mixing the solution till it is homogenized. Preferably, the spraying of a solution or dispersion onto sugar spheres or drug coated pellets in the method uses a fluidized bed coater with a Wurster insertion. Furthermore, the binder, used in coating the sub-coated sugar spheres with a drug layer, facilitates binding of the drug to the inert core of sub-coated sugar spheres. Moreover, in this method the ratio of powder mixture to controlled release drug coated pellets in the final tableting blend is preferably from about 20% to about 60% (by weight), more preferably from about 30% to about 50% (by weight), most preferably from about 35% to about 45% (by weight). As a result a uniform final tableting blend and tablets are produced.

Third Extended Release Coating

An extended release phase may comprise at least one high viscosity hypromellose (HPMC) ingredient. HPMC is a water soluble matrix-forming polymer used to provide an extended release effect of metoprolol. The viscosity of the HPMC used in the ER phase may be up to 100.000 centipoise such as in the range of about 3500-6000 cps.

An extended release layer with a therapeutically effective amount of a beta blocker, such as metoprolol or carvedilol, can be made with high viscosity hypromellose alone.

In other embodiments, the extended release layer comprises a therapeutically effective amount of a beta blocker, such as metoprolol or carvedilol, at least one high viscosity hypromellose, at least one binding agent, a low viscosity hypromellose, at least one modified starch, and optionally one or more other pharmaceutically acceptable intragranular components including but not limited to a second pharmaceutically acceptable active ingredient, other pharmaceutically acceptable excipients and/or adjuvants. In one embodiment, the ratio of high-viscosity hypromellose to low viscosity hypromellose is about 3.3 to about 0.85. In another embodiment the ratio of high to low is about 3:1.

Suitably, the viscosity of the low viscosity hypromellose is in the range of about 10-30 centipoises. In another embodiment the low viscosity is about 15 centipoises.

The amount of at least one binding agent in the extended release phase of a bilayer tablet may be from about 0.5% to about 3% w/w. In one embodiment there are at least two binding agents present in the ER phase. Suitably the amount of at least one modified starch in the extended release phase of the bilayer tablet is from about 0.5% to about 3% w/w. In one embodiment, the amount of modified starch is about 1% w/w of the ER phase. In one embodiment there are at least two modified starches present in the ER phase. Suitably, the modified starch is pre-gelatinized.

Suitably, the amount of the high viscosity hypromellose present in the extended release phase is from about 3%> to about 7%> of the extended release phase formulation weight. In another embodiment, the amount of high viscosity hypromellose is from about 4% to about 6%. In still other embodiments, an amount of >20% hypromellose is used in the extended release phase.

In yet another embodiment the amount of high viscosity HPMC is present in an amount of about 5% w/w extended release phase formulation weight.

Suitably, the amount of the low viscosity hypromellose present in the extended release phase is from about 0.5% to about 3% of the extended release phase formulation weight. In another embodiment, the amount of low viscosity hypromellose is from about 1% to about 2% of the extended release phase formulation weight.

Alternatively, the total amount of cellulosic derivatives of HPMC present in the ER granulate range from about 3% to about 10% by weight of the total amount of extended release components. This encompasses both the high and the low viscosity HPMC's.

In one embodiment the ER phase comprises metoprolol, povidone, pre-gelatinized corn starch, and a high and low viscosity HPMC.

In one embodiment the ER phase comprises carvedilol, povidone, pre-gelatinized corn starch, and a high and low viscosity HPMC.

Tablets and Capsules

The film coated beads or spheres may be provided in sachets or formulated as a capsule, for example a hard gelatin capsule, or compressed to form tablets using known methods with the optional addition of other pharmaceutically acceptable additives and with the addition of the beta blocker IR and tesofensine components herein described. Coated beads to be compressed into a tablet are obtained by conventional techniques known to those skilled in the art.

Also, during this process suitable other agents can be added. For example, during the tabletting step suitable fillers, eg microcrystalline cellulose, lactose monohydrate, talc. sodium stearyl fumarate etc can be utilised to give acceptable compression characteristics of the formulation, e g hardness of the tablet.

These additives can be granulated in one of the conventional granulation methods. However, preferably there is provided a set of additives, for example a powder mixture that can be directly compressed into tablets. Such powder mixture serves as a filler, cushioning, disintegrant, glidant, and lubricant mixture. Furthermore, the ratio of controlled release drug coated pellets to additives in the final (e.g. tableting) blend of the present pharmaceutical composition is of particular importance to prepare a uniform product e.g. tablets.

To prepare a uniform product, preferably at least 50% (by weight) of the powder mixture may have particle sizes between about 30 μm to about 800 μm, preferably from about 80 μm to about 600 μm, more preferably from about 100 μm to about 300 μm. More preferably, at least 65% (by weight) of the powder mixture has particle sizes between about 30 μm to about 800 μm, preferably from about 80 μm to about 600 μm, more preferably from about 100 μm to about 300 μm. Most preferably, at least 80% (by weight) of the powder mixture has particle sizes between about 30 μm to about 800 μm, preferably from about 80 μm to about 600 μm, most preferably from about 100 μm to about 300 μm.

Furthermore, the amount of controlled release drug coated pellets in the final tableting blend is preferably from about 20% to about 60% (by weight) in order to prepare such uniform product. More preferably, the amount of controlled release drug coated pellet in the final tableting blend is from about 30% to about 50% (by weight), most preferably from about 35% to about 45% (by weight).

Suitable powder mixtures comprise, but are not limited to, mixtures of two or more of the following compounds; Starlac® (a spray-dried compound consisting of 85% alpha-lactose monohydrate and 15% maize starch dry matter available from Meggle), Cellactose® (a spray-dried compound consisting of 75% alpha-lactose monohydrate and 25% cellulose powder dry matter available from Meggle), Parteck® (A Directly Compressible Sorbitol available from Merck KGaA), Crospovidone, Silicon Dioxide, Magnesium Stearate, Talc, Zinc Stearate, Polyoxyethylene Stearate, Stearic Acid, sodium stearyl fumarate Cellulose derivatives, microcrystalline cellulose and lactose monohydrate.

If the dosage form is a bi- or tri-layer tablet, the immediate release layer(s) may be compressed directly on a previously partly compressed extended release layer, or alternatively, the extended release layer may be compressed onto previously partly compressed immediate release layer(s).

The compositions can be formulated by conventional methods of admixture such as granulating, blending, filling and compressing. For example, tablets can be produced by a wet granulation process, where the immediate release phase and extended release phase are separately prepared. Suitably, for either the immediate release or extended release phase, the active drug substance and excipients are screened and mixed in a high shear mixer granulator or fluid bed dryer. The blend is granulated by the addition of a granulating solution (typically purified water, disintegration agent dissolved/dispersed in purified water, or drug dissolved/dispersed in purified water or a suitable solvent) sprayed into the high shear mixer granulator or fluid bed dryer. If desired wetting agents e.g., surfactants can be added. The resulting granules (optionally pelletized) are dried usually with residual moisture of 1-5% by tray, fluid bed or microwave drying techniques. The dried granules are milled to produce a uniform particle size, the granules are blended with extragranular excipients as necessary, typically a lubricant and glidant (e.g., magnesium stearate, silicon dioxide). The separately prepared immediate release and extended release granules can then be compressed together using a rotary tablet press (such as a bilayer tablet press) if desired. If the dosage form is a single layer tablet, then the extended release granules are admixed with the immediate release extragranular components and compressed together using a rotary tablet press, etc. These resulting tablets can all be coated in a pan coater typically with a 1-5% aqueous film coat, followed by a wax polishing.

Alternatively tablets can be produced by a direct compression process. Suitably the active drug substance and excipients for the immediate release and extended release phases are separately screened and mixed in a suitable blender e.g., a cone, cube or V-blender. Other excipients are added as necessary, and further blended. The separately prepared immediate release and extended release phases can be combined and compressed together using a rotary tablet press as hereinbefore described. The resulting tablets can be coated in a pan coater.

Tablets can also be prepared by using both methods of wet granulation and direct compression. For example the extended release phase can be prepared by wet granulation as described herein, while the immediate release phase can be prepared by blending the excipients for direct compression. The two phases can then be combined and compressed together as hereinbefore described.

Immediate Release Phase(s)

The immediate release phase(s) may be prepared by combining a directly compressible commercially available grade of the beta blocker, such as metoprolol, and tesofensine with a lubricant, and one or more disintegrating agents if necessary or desired. Binders and other excipients and/or adjuvants may be included in the immediate release layer(s), also if necessary or desired. The beta blocker and tesofensine in the immediate release layer may be combined with a modified starch such as a pre-gelatinized starch, e.g., corn starch, polyethylene glycol, and a disintegrant, or super disintegrant such as croscarmellose sodium or Explotab®, a binder such as methylcellulose or hypromellose polymer, plasticizer, pigment and a lubricant.

The immediate release phases may comprise two different layers of the beta blocker and tesofensine, respectively. Alternatively, the immediate release phases may be combined into one and the same layer. The immediate release phases may also be formulated into an extragranular phase of a tablet or be granulated into one or two different immediate release granules. For tesofensine, the preferred formulation is a granulation of tesofensine compared to direct compression of tesofensine as the dose is relatively low.

Monolith Dosage Form

In one embodiment, there is only a single layer tablet having an extended release intra-granular phase and two immediate release extra-granular phases. The extended release phase will be comprised of an intra-granular component of the beta blocker and excipients as described above. These components form the ER granulate. The ER blend could be made into pellets and compressed accordingly with the extra-granular immediate release blend.

A suitable extra-granular component or phase, i.e., the immediate release phases, may be prepared by combining a directly compressible commercially available grade of a beta blocker, such as metoprolol, and tesofensine citrate with a lubricant, and one or more disintegrating agents if necessary or desired. As mentioned above for tesofensine the preferred process is to prepare a granulate of tesofensine before compression. Binders and other excipients and/or adjuvants may be included in the extra-granular phase if necessary or desired. Alternatively, an extra-granular component can be prepared by combining the beta blocker, such as metoprolol, and tesofensine with a modified starch, such as a pre-gelatinized starch, e.g., corn starch, a disintegrant or super disintegrant, such as croscarmellose sodium, a binder and a lubricant.

Excipients

The present compositions may include components that functions as a binder or binding agent. Suitably, the binding agent may comprise a first binding agent and a second binding agent. Suitable binding agents for use herein include conventional binding agents used in the art such as gelatin, starches, povidone, polymers and cellulose derivatives or combinations thereof.

Suitably, the starch, is of vegetable origin, such as corn (or maize) starch, modified corn starch, wheat starch, modified wheat starch, potato starch, or pre-gelatinized starch e.g., available commercially as Starch 1500 G or Prejel; or a combination of two or more thereof.

If the binding agent includes a cellulosic derivative such as hydroxypropyl cellulose (HPC) (of low to medium viscosity) e.g., as may be available commercially under the brand name Klucel® from the Aqualon division of Hercules Inc., Dow Chemical Company e.g., Klucel GF, Klucel JF, Klucel LF and Klucel EF; microcrystalline cellulose (MCC), carboxymethylcellulose (MC), sodium carboxymethylethyl cellulose; or a combination of two or more thereof. Combinations of a cellulosic derivative with other binding agents noted above are also envisaged. Generally the total amount of cellulosic derivatives present in the granulate are in an amount ranging from about 3% to about 10% by weight of the extended release components. It is recognized in the art that certain cellulosic derivatives, such as hypromellose, will have varying roles in a formulation, depending upon the amount used. For example hypromellose (low or medium viscosity) may function as a binding agent, a coating agent, or as a matrix forming agent.

While a binding agent is present as an intra-granular component, it is recognized that a modest amount of binding agent e.g., up to about an additional 3.0%>–10.0% by weight of the intra-granular binding agent content of the composition, may also be present extra-granularly.

In one embodiment, suitably the starch is pre-gelatinized starch. Pre-gelatinized starch is a starch that has been chemically and/or mechanically processed. Typically pre-gelatinized starch contains 5% of free amylase, 15% of free amylopectin, and 80% unmodified starch. Pre-gelatinized starch may be obtained from corn (or maize), potato or rice starch.

The granulate provides an intimate admixture of a combination of ingredients and may then be mixed with one or more pharmaceutically acceptable extra-granular components of the composition i.e., with any pharmaceutically acceptable ingredient e.g., a diluent, flavor, sweetening agent, binder, disintegrant, glidant, lubricant, anti-adherent, anti-static agent, anti-oxidant, desiccant, or a second pharmaceutically acceptable active agent. It is recognized that these same ingredients may be present both as an intra-granular and as an extra-granular ingredient.

As noted above there are other inactive ingredients that may optionally be employed in relatively small quantities, which include lubricants, flow agents, and binders that facilitate compression.

Suitable disintegrating agents include a non-super disintegrant, a super disintegrant or a combination of both. Suitable non-super disintegrants include conventional disintegrants such as starch (corn or maize), pre-gelatinized starch e.g., Starch 1500 G, clays (e.g. VEEGUM (Vanderbilt Minerals, LLC) or Bentonite (an absorbent aluminium phyllosilicate clay consisting mostly of montmorillonite)), microcrystalline cellulose, cellulose or powdered cellulose. It is recognized in the art, that some excipients may perform more than one role in a given pharmaceutical formulation. For example certain excipients, e.g., starches including pre-gelatinized starch, and microcrystalline cellulose (hereinbefore identified as binding agents) function as both binders and disintegrants.

A "super disintegrant" represents a class of disintegrating agent which may generally be used in lower amounts in pharmaceutical preparations, as compared to conventional disintegrants. Examples of super disintegrants include sodium starch glycolate, the sodium salt of carboxymethyl starch, modified cellulose and cross-linked polyvinyl pyrrolidone. Sodium starch glycolate is available commercially under the trade names Explotab® (Edward Mendell Co. JRS Pharma), Primojel® (Generichem Corp; DFE Pharma) and Tablo® (Blanver, Brazil). An example of modified cellulose includes croscarmellose sodium, the sodium salt of carboxymethyl cellulose. Croscarmellose sodium is available commercially under the trade names AcDiSol® (FMC Corp.), Nymcel ZSX® (Nyma, Netherlands), Primellose® (Avebe, Netherlands), Solutab® (Blanver, Brazil). An example of a cross-linked polyvinyl pyrrolidone includes crospovidone, and is commercially available under the trade names Kollidon CL® or Kollidon CL-M (Basf Corp.), and Polyplasdone XL® (ISP Corp; Ashland). A suitable super disintegrants includes croscarmellose sodium or sodium starch glycolate (e.g. Explotab® (JRS Pharma)) or a combination thereof. A super disintegrant may be used extra-granularly, in an amount ranging from about 0.5% to about 5.0% by weight of the composition. Suitable preservative or antimicrobial agents for use include potassium sorbate or a paraben, i.e., one or more hydroxy benzoic acid esters e.g., methyl, ethyl, propyl or butyl, suitably singularly or as mixtures. Parabens are commercially available under the Nipa® brand name, e.g., Nipasept® sodium (Aako BV, The Netherlands).

Suitable lubricants include magnesium, calcium or sodium stearate, stearic acid or talc that may be added in suitable amounts. In one embodiment the lubricant is magnesium stearate.

Suitable flow agents include silicon dioxide (e.g. Cab-O-Sil® (Cabot Corporation), Syloid™ (W.R. Grace & Co.)) and colloidal silicon dioxide (Aerosil® (Evonik Resource Efficiency GmbH)), that may be added in an amount from about 0.5% to about 1% by weight.

The compressed tablet may further comprise a film coat e.g., hypromellose or polyvinyl alcohol-part.hydrolised (PVA). Suitably the film coat is a transparent film coat e.g., a dye, although an opaque film coat e.g., as obtained when using a film coat in combination with an opacifier or a pigment such as titanium dioxide or a lake may also be used.

For example one commercially available film coat is an Opadry® coating system from Colorcon.

Medical Use

The composition as described herein is useful as a medicament, e.g. for the treatment, prevention or alleviation of obesity and/or an obesity associated disorder.

Due to the particular combination of extended and immediate release forms of a beta blocker in combination with tesofensine as described herein the composition of the present disclosure effectively alleviates cardiovascular side-effects of tesofensine while maintaining the therapeutic efficacy of tesofensine.

In one embodiment the composition of the present disclosure is for use as a medicament.

In one embodiment the composition of the present disclosure is for use in the treatment of obesity.

Obesity is defined herein as a medical condition in which excess body fat has accumulated to the extent that it may have an adverse effect on health, leading to reduced life expectancy and/or increased health problems in general. Thus, in one embodiment the subject to be treated with the composition of the present disclosure is obese.

Body mass index (BMI) is a measure which compares weight and height. People are generally considered overweight or pre-obese if the BMI is between 25 and 30 and obese if the BMI is over 30. Morbidly obese subjects have a BMI over 35.

In one embodiment the subject has a BMI above 25 kg/m$^2$, such as above 30 kg/m$^2$, for example above 35 kg/m$^2$, such as above 40 kg/m$^2$.

In one embodiment the subject has a BMI above 30 kg/m$^2$.

In one embodiment the subject has a BMI above 35 kg/m$^2$.

In one embodiment the composition of the present disclosure is for use in the treatment of an obesity associated disorder, such as a disease or disorder selected from the group consisting of diabetes, metabolic syndrome, dyslipidemia, atherosclerosis, drug-induced obesity, overeating disorders, bulimia nervosa, binge eating disorder, compulsive over-eating, impaired appetite regulation, nonalcoholic fatty liver disease (NAFLD) and nonalcoholic steatohepatitis (NASH).

In one embodiment the composition of the present disclosure is for use in the treatment of diabetes, such as type 1 diabetes, type 2 diabetes, prediabetes and gestational diabetes. Preferably, the diabetic subject is obese.

In one embodiment the composition of the present disclosure is for use in the treatment of type 1 diabetes.

In one embodiment the composition of the present disclosure is for use in the treatment of type 2 diabetes.

In one embodiment the composition of the present disclosure is for use in the treatment of prediabetes.

In one embodiment the composition as described herein leads to an alleviation or improvement of diabetic complications.

Type 1 diabetes (diabetes mellitus type 1) is a form of diabetes that results from the autoimmune destruction of the insulin-producing beta cells in the pancreas. In type 1 diabetes, hypertension may reflect the onset of diabetic nephropathy.

Type 2 diabetes is a metabolic disorder that is characterized by hyperglycemia in the context of insulin resistance and a relative lack of insulin. Type 2 diabetes makes up about 90% of cases of diabetes, with the other 10% due primarily to diabetes mellitus type 1 and gestational diabetes. Obesity is thought to be the primary cause of type 2 diabetes in people who are genetically predisposed to the disease.

Pre-diabetes is used interchangeably herein with intermediate hyperglycaemia. Intermediate hyperglycaemia is a biochemical state in which a person has glucose levels above the normal range, but does not yet meet the criteria for a diagnosis of diabetes. The primary aim of management of intermediate hyperglycaemia is to prevent progression to diabetes.

A pre-diabetic subject may have one or more of impaired fasting glycaemia (IFG) and/or impaired glucose tolerance (IGT) and/or elevated glycated haemoglobin (HbA$_{1c}$) levels.

Weight loss can prevent progression of pre-diabetes into diabetes and can also markedly improve clinical symptoms of type 2 diabetes. Thus, weight loss is an attractive treatment strategy for pre-diabetic subjects and subjects suffering from type 2 diabetes.

In one embodiment the subject is an obese, pre-diabetic human. In one embodiment the subject is an obese subject suffering from type 2 diabetes.

Gestational diabetes is a condition in which women without previously diagnosed diabetes exhibit high blood glucose levels during pregnancy (especially during their third trimester). Gestational diabetes is caused when insulin receptors do not function properly.

The WHO diabetes diagnostic criteria are shown in the table below.

| Condition | 2 hour glucose* mmol/l (mg/dl) | Fasting glucose mmol/l (mg/dl) | HbA$_{1c}$ mmol/mol (DCCT %) |
|---|---|---|---|
| Normal | <7.8 (<140) | <6.1 (<110) | <42 (<6.0) |
| Impaired fasting glycaemia | <7.8 (<140) | ≥6.1 (≥110) & <7.0 (<126) | 42-46 (6.0-6.4) |
| Impaired glucose tolerance | ≥7.8 (≥140) | <7.0 (<126) | 42-46 (6.0-6.4) |
| Diabetes mellitus | ≥11.1 (≥200) | ≥7.0 (≥126) | ≥48 (≥6.5) |

*Venous plasma glucose 2 hours after ingestion of 75 g oral glucose load

The subject benefitting from treatment with the composition of the present disclosure may also be a subject suffering from an obesity-associated disorder or condition, such as one selected from the group consisting of diabetes, metabolic syndrome, dyslipidemia, atherosclerosis, drug-induced obesity, overeating disorders, bulimia nervosa, binge eating disorder, compulsive over-eating, impaired appetite regulation, nonalcoholic fatty liver disease (NAFLD) and nonalcoholic steatohepatitis (NASH).

In one embodiment the composition of the present disclosure is for use in the treatment of metabolic syndrome, such as for the treatment of an obese subject suffering from metabolic syndrome.

In one embodiment the composition of the present disclosure is for use in the treatment of fatty liver disease, such as nonalcoholic fatty liver disease (NAFLD) or nonalcoholic steatohepatitis (NASH). The subject suffering from NAFLD or NASH is preferably obese.

In one embodiment, the composition of the present disclosure is for use in the treatment of nonalcoholic fatty liver disease (NAFLD).

In one embodiment, the composition of the present disclosure is for use in the treatment of nonalcoholic steatohepatitis (NASH).

Nonalcoholic fatty liver disease (NAFLD) is a cause of a fatty liver, occurring when fat is deposited in the liver (steatosis) due to other causes than excessive alcohol use. NAFLD is the most common liver disorder in Western industrialized nations. NAFLD is associated with insulin resistance and metabolic syndrome (obesity, combined hyperlipidemia, diabetes mellitus (type II) and high blood pressure). Non-alcoholic steatohepatitis (NASH) is the most extreme form of NAFLD, and is a major cause of cirrhosis of the liver. NASH is a state in which the steatosis is combined with inflammation and fibrosis (steatohepatitis).

In one embodiment the composition of the present disclosure is for use in a method of decreasing liver fat and/or visceral adiposity. Reduction of liver fat and/or visceral adiposity has been shown to be effective in the treatment of fatty liver disorders. Tesofensine significantly decreases waist circumference and sagittal diameter (Astrup et al., 2008, Lancet 372: 1906-13); hence tesofensine is capable of reducing visceral adiposity.

The composition of the present disclosure is preferably administered to a subject in need thereof once a day. However, in certain embodiments, the composition may be administered more than once a day, such as twice a day or alternatively less than once a day, such as once every second or third day depending on the specific formulation and concentration of the individual components of the composition.

The subject treated is preferably a human, such as an adult human aged 18 or older.

In one embodiment the present disclosure relates to use of the composition as disclosed herein in the manufacture of a medicament for the treatment of diabetes, obesity or an obesity associated disorder.

The following non-limiting Examples illustrate the advantageous properties of the compositions.

EXAMPLES

Example 1

Take controlled release Metoprolol succinate pellets produced as described in WO 2007/097770 with a potency of 51.19% Metoprolol succinate (corresponding to 53.88% Metoprolol tartrate) and mix with microcrystalline cellulose, lactose monohydrate, croscarmellose sodium and magnesium stearate. The mix is compressed to tablets on a rotary tablet press, each tablet with a tablet weight of 400 mg and size 7×14 mm each holding 100 mg Metoprolol tartrate equivalents. Tablets will release the drug in a zero order release rate.

| | |
|---|---|
| Metoprolol succinate pellets | 371.2 |
| Microcrystalline cellulose | 240.0 |
| Lactose monohydrate | 164.8 |
| Croscarmellose sodium | 16.0 |
| Magnesium stearate | 8.0 |
| Total | 800.0 |

Metoprolol 100 mg ER tablets (containing 95 mg Metoprolol succinate) are film coated in a perforated drum coater with an aqueous film containing Tesofensine citrate. Film composition is given in the table. 125 mg of film solution is applied for each tablet corresponding to an increase in tablet weight of approx. 2.2%. Spraying conditions are controlled to an outlet air temperature of 40-45° C.

| | |
|---|---|
| Methocel E 15 | 12.0 |
| Polyethylene glycol 6000 | 1.2 |
| Tesofensine citrate | 0.8 |
| Water | 186.0 |
| Total | 200.0 |

The sub coated Metoprolol tablets are further coated with the final coating solution given in the next table. 250 mg of film solution is applied for each tablet corresponding to an increase in tablet weight of approx. 16.0%. Spraying conditions are controlled to an outlet air temperature of 43-48° C. The final product contains 100 mg of ER metoprolol and 25 mg of IR metoprolol.

| | |
|---|---|
| OPADRY ® II Complete Film Coating System 85F18422 White | 50.0 |
| Metoprolol succinate | 28.5 |
| Water | 221.5 |
| Total | 300.0 |

Example 2

As example 1, but with the Metoprolol film as sub coating and the Tesofensine coating as final coating.

Example 3

As example 1, but using Metoprolol controlled release pellets as described in U.S. Pat. No. 7,959,947, example 3 by AstraZeneca.

Example 4

Metoprolol pellets are prepared by mixing Metoprolol succinate with microcrystalline cellulose and adding water in a high shear mixer until proper moistening is achieved. The wet mass is extruded through a Bepex extruder and the form strings are rolled to squares on a spheronizer. The resulting pellets of about 1 mm in diameter are dried in a fluid-bed at 60° C. inlet air temperature. The Metoprolol pellets are film coated in a fluid-bed with bottom spray with a film to control the release pattern. Approx. 5% weight increase is anticipated.

| | |
|---|---|
| Metoprolol succinate | 311 g |
| Microcrystalline cellulose | 289 g |
| Water | 200 g |
| Total | 800.0 |

| | |
|---|---|
| Ethylcellulose 7 cps | 6.75 g |
| Methocel E 15 | 0.75 g |
| Ethanol 96% | 69.375 g |
| Water | 23.125 |
| Total | 100.0 |

Core tablets are produced from the batch composition in example 1 with a core tablet weight of 400 mg. Sub coating and final coating are applied as described in example 1. The final product is a tablet with 100 mg of ER metoprolol and 25 mg of IR metoprolol.

Example 5

Tesofensine citrate and microcrystalline cellulose are mixed for 20 minutes. Metoprolol succinate, rest of the microcrystalline cellulose and silicon dioxide, colloidal are mixed in for another 20 minutes. Controlled release Metoprolol pellets as described in example 1 are added to the blend and mixed with for 20 minutes. The blend is filled into hard gelatine capsules size 1.

| | |
|---|---|
| Metoprolol succinate | 23.75 g |
| Tesofensine citrate | 0.50 g |
| Microcrystalline cellulose | 88.65 g |
| Silicon dioxide, colloidal | 1.50 g |
| Controlled release Metoprolol pellets 53.88% | 185.60 g |
| Total | 300 g |

The final product is a gelatine capsule with 100 mg of ER metoprolol and 25 mg of IR metoprolol.

Example 6

Metoprolol ER tablet with separate film coatings of Tesofensine and metoprolol IR.

Metoprolol 100 mg ER tablets from example 1 (containing 95 mg Metoprolol succinate) were film coated in a perforated drum coater with an aqueous film containing Tesofensine citrate. Film composition is given in the table. 370.4 mg of film solution was applied for each tablet corresponding to an increase in tablet weight of approx. 4.2%. Spraying conditions were controlled to an outlet air temperature of 45-50° C.

| | |
|---|---|
| Methocel E 15 | 8.0 |
| Polyethylene glycol 6000 | 0.8 |
| Tesofensine citrate | 0.27 |
| Water | 190.93 |
| Total | 200.0 |

The sub coated Metoprolol tablets were further coated with the final coating solution given in the next table. 312.5 mg of film solution was applied for each tablet corresponding to an increase in tablet weight of approx. 15.7%. Spraying conditions were controlled to an outlet air temperature of 46-49° C.

| | |
|---|---|
| OPADRY ® COMPLETE FILM COATING SYSTEM 03F180011 WHITE | 26.667 |
| Metoprolol succinate | 15.2 |
| Water | 158.133 |
| Total | 200.0 |

The release of Metoprolol was tested according to the USP monograph for Metoprolol Succinate Extended-Release Tablets, Test 1 (The United States Pharmacopeial Convention, Official Aug. 1, 2012). Results were:

| Time (h) | Amount dissolved (%) |
|---|---|
| 1 | 23 |
| 4 | 29 |
| 8 | 47 |
| 20 | 102 |

Tesofensine release was tested at the one-hour time point and found to have released fully.

The release profile of Metoprolol from Metoprolol 100 mg ER 25 mg IR tablets with separate Tesofensine—and Metoprolol IR films applied is shown in FIG. 3.

Example 7

Metoprolol ER tablet with film coating containing both Tesofensine and metoprolol IR.

Metoprolol 100 mg ER tablets from example 1 (containing 95 mg Metoprolol succinate) were film coated in a perforated drum coater with an aqueous film containing Tesofensine citrate plus Metoprolol succinate. Film composition is given in the table. 312.5 mg of film solution was applied for each tablet corresponding to an increase in tablet weight of approx. 16.5%. Spraying conditions were controlled to an outlet air temperature of 45-50° C.

| | |
|---|---|
| OPADRY ® COMPLETE FILM COATING SYSTEM 03F180011 WHITE | 30.00 |
| Metoprolol succinate | 17.10 |
| Tesofensine citrate | 0.36 |
| Water | 177.54 |
| Total | 225.0 |

The release of Metoprolol was tested according to the USP monograph for Metoprolol Succinate Extended-Release Tablets, Test 1 (The United States Pharmacopeial Convention, Official Aug. 1, 2012). Results were:

| Time (h) | Amount dissolved (%) |
|---|---|
| 1 | 24 |
| 4 | 35 |
| 8 | 55 |
| 20 | 105 |

Tesofensine release was tested at the one-hour time point and found to have released fully.

The release profile of Metoprolol from Metoprolol 100 mg ER and 25 mg IR tablets with combined Tesofensine/Metoprolol film applied is shown in FIG. 3.

Example 8

Carvedilol 80 mg ER tablets with separate coatings of Tesofensine and carvedilol IR.

The tablets contain 0.5 mg IR Tesofensine, 80 mg ER Carvedilol and 20 mg IR Carvedilol, i.e. the ER:IR ratio is 80:20.

Carvedilol 400 mg/g pellets are prepared by mixing Carvedilol with microcrystalline cellulose and adding water in a high shear mixer until proper moistening is achieved. The wet mass is extruded through a Bepex extruder and the form strings are rolled to squares on a spheronizer. The resulting pellets of about 1 mm in diameter are dried in a fluid-bed at 60° C. inlet air temperature. The carvedilol pellets are film coated in a fluid-bed with bottom spray with a film to control the release pattern. Approx. 5% weight increase is anticipated.

| | |
|---|---|
| Carvedilol | 252 g |
| Microcrystalline cellulose | 348 g |
| Water | 200 g |
| Total | 800.0 |

| | |
|---|---|
| Ethylcellulose 7 cps | 6.75 g |
| Methocel E 15 | 0.75 g |
| Ethanol 96% | 69.375 g |
| Water | 23.125 |
| Total | 100.0 |

Carvedilol 80 mg ER tablets are produced by mixing Carvedilol 400 mg/g pellets with microcrystalline cellulose, lactose monohydrate, croscarmellose sodium and magnesium stearate. The mix is compressed to tablets on a rotary tablet press, each tablet with a tablet weight of 400 mg and size 7×14 mm each holding 80 mg Carvedilol. Tablets will release the drug in a zero order release rate.

| | |
|---|---|
| Carvedilol 400 mg/g pellets | 400.0 |
| Microcrystalline cellulose | 240.0 |
| Lactose monohydrate | 135.8 |
| Croscarmellose sodium | 16.0 |
| Magnesium stearate | 8.0 |
| Total | 800.0 |

Carvedilol 80 mg ER tablets are film coated in a perforated drum coater with an aqueous film containing Tesofensine citrate. Film composition is given in the table. 370.4 mg of film solution is applied for each tablet corresponding to an increase in tablet weight of approx. 4.2%. Spraying conditions were controlled to an outlet air temperature of 45-50° C.

| | |
|---|---|
| Methocel E 15 | 8.0 |
| Polyethylene glycol 6000 | 0.8 |
| Tesofensine citrate | 0.27 |
| Water | 190.93 |
| Total | 200.0 |

The sub coated Carvedilol/Tesofensine tablets are further coated with the final coating dispersion given in the next table. 313.6 mg of film solution is applied for each tablet corresponding to an increase in tablet weight of approx. 14.8%. Spraying conditions are controlled to an outlet air temperature of 46-49° C. The amount of Carvedilol in the IR film coating corresponds to 20 mg Carvedilol.

| | |
|---|---|
| OPADRY ® COMPLETE FILM COATING SYSTEM 03F180011 WHITE | 26.667 |
| Carvedilol | 12.7536 |
| Water | 160.579 |
| Total | 200.0 |

Figure 4:
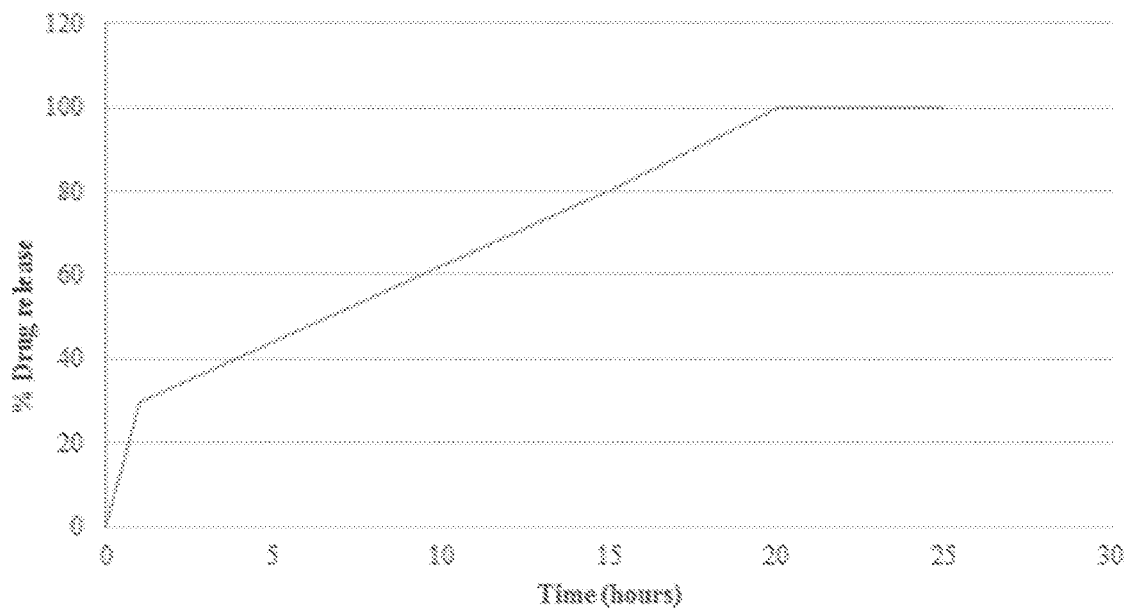
FIG. 4: The expected dissolution profile for Carvedilol in a pharmaceutical product comprising 80 mg extended release Carvedilol and 20 mg immediate release Carvedilol

The expected dissolution profile for Carvedilol in a pharmaceutical product comprising 80 mg extended release Carvedilol and 20 mg immediate release Carvedilol is depicted in FIG. 4. The dissolution profile is measured using a USP type 1 dissolution instrument using 500 ml pH 1.45 for two hours and then increasing pH to 7 and volume to 900 ml. The test is performed at 37° C. with 50 rpm stirring for 20 hours.

Example 9

Carvedilol 40 mg ER tablets with separate coatings of Tesofensine and carvedilol IR.

The tablets contain 0.5 mg IR Tesofensine, 40 mg ER Carvedilol and 10 mg IR Carvedilol, i.e. the ER:IR ratio is 80:20.

Carvedilol 40 mg ER tablets are produced by mixing Carvedilol 400 mg/g pellets (from example 8) with microcrystalline cellulose, lactose monohydrate, croscarmellose sodium and magnesium stearate. The mix is compressed to tablets on a rotary tablet press, each tablet with a tablet weight of 400 mg and size 7×14 mm each holding 40 mg Carvedilol. Tablets will release the drug in a zero order release rate.

| | |
|---|---|
| Carvedilol 400 mg/g pellets | 200.0 |
| Microcrystalline cellulose | 320.0 |
| Lactose monohydrate | 255.8 |
| Croscarmellose sodium | 16.0 |
| Magnesium stearate | 8.0 |
| Total | 800.0 |

Carvedilol 40 mg ER tablets are film coated in a perforated drum coater with an aqueous film containing Tesofensine citrate. Film composition is given in the table. 370.4 mg of film solution is applied for each tablet corresponding to an increase in tablet weight of approx. 4.2%. Spraying conditions were controlled to an outlet air temperature of 45-50° C.

| | |
|---|---|
| Methocel E 15 | 8.0 |
| Polyethylene glycol 6000 | 0.8 |
| Tesofensine citrate | 0.27 |
| Water | 190.93 |
| Total | 200.0 |

The sub coated Carvedilol 40 mg ER/Tesofensine tablets are further coated with the final coating dispersion given in the next table. 313.6 mg of film solution is applied for each tablet corresponding to an increase in tablet weight of approx. 12.4%. Spraying conditions are controlled to an outlet air temperature of 46-49° C. The amount of Carvedilol in the IR film coating corresponds to 10 mg Carvedilol.

| | |
|---|---|
| OPADRY ® COMPLETE FILM COATING SYSTEM 03F180011 WHITE | 26.667 |
| Carvedilol | 6.3768 |
| Water | 166.956 |
| Total | 200.0 |

The expected dissolution profile for Carvedilol in a pharmaceutical product comprising 40 mg extended release Carvedilol and 10 mg immediate release Carvedilol is depicted in FIG. 4. The dissolution profile is measured using a USP type 1 dissolution instrument using 500 ml pH 1.45 for two hours and then increasing pH to 7 and volume to 900 ml. The test is performed at 37° C. with 50 rpm stirring for 20 hours.

What is claimed:

1. A method of effectively treating an overeating disorder, a binge eating disorder, compulsive over-eating, or impaired appetite regulation, in a subject comprising orally administering to the subject, once daily, a capsule comprising:
   0.1 to 1 mg of tesofensine or a pharmaceutically acceptable salt thereof; and
   a beta blocker that is metoprolol or a pharmaceutically acceptable salt thereof in an amount up to 250 mg; and
   wherein the beta blocker comprises:
      an extended release part and an immediate release part; and
   wherein the ratio of the amount of beta blocker in the extended release part to the amount of beta blocker in the immediate release part is from 75:25 to 95:5; and
   wherein the administration does not produce tesofensine-induced cardiovascular side-effects.

2. The method of claim 1, wherein the pharmaceutical dosage form comprises tesofensine free base, tesofensine citrate salt, or tesofensine tartrate salt.

3. The method of claim 1, wherein the pharmaceutical dosage form comprises 0.2 mg to 0.8 mg of the tesofensine or a pharmaceutically acceptable salt thereof.

4. The method of claim 1, wherein the pharmaceutical dosage form comprises 0.25 mg to 0.75 mg of the tesofensine or a pharmaceutically acceptable salt thereof.

5. The method of claim 1, wherein the pharmaceutical dosage form comprises about 0.4 mg to about 0.6 mg of the tesofensine or a pharmaceutically acceptable salt thereof.

6. The method of claim 1, wherein the pharmaceutical dosage form comprises 5 mg to 10 mg of the beta blocker in the immediate release part.

7. The method of claim 1, wherein the ratio of the beta blocker in the extended release part to the beta blocker in the immediate release part in the pharmaceutical dosage form is 75:25.

8. The method of claim 1, wherein the ratio of the beta blocker in the extended release part to the beta blocker in the immediate release part in the pharmaceutical dosage form is 80:20.

9. The method of claim 1, wherein the ratio of the beta blocker in the extended release part to the beta blocker in the immediate release part in the pharmaceutical dosage form is 90:10.

10. The method of claim 1, wherein the ratio of the beta blocker in the extended release part to the beta blocker in the immediate release part in the pharmaceutical dosage form is 95:5.

11. The method of claim 1, wherein the pharmaceutical dosage form comprises 50 mg to 200 mg of the beta blocker in the extended release part and 5 mg to 50 mg of the beta blocker in the immediate release part.

12. The method of claim 1, wherein the pharmaceutical dosage form comprises 75 mg to 125 mg of the beta blocker in the extended release part and 10 mg to 25 mg of the beta blocker in the immediate release part.

13. The method of claim 1, wherein the pharmaceutical dosage form comprises 75 mg to 80 mg of the beta blocker in the extended release part and 10 mg to 15 mg of the beta blocker in the immediate release part.

14. The method of claim 1, wherein the extended release part of the beta blocker in the pharmaceutical dosage form comprises a pellet comprising an inert pellet core; a drug layer comprising the beta blocker; and a controlled release layer thereon.

15. The method of claim 1, wherein the medical condition is an overeating disorder.

16. The method of claim 1, wherein the medical condition is a binge eating disorder.

17. The method of claim 1, wherein the medical condition is compulsive over-eating.

* * * * *

UNITED STATES PATENT AND TRADEMARK OFFICE
CERTIFICATE OF CORRECTION

PATENT NO. : 11,426,383 B2
APPLICATION NO. : 17/066843
DATED : August 30, 2022
INVENTOR(S) : Peter G. Nielsen, Mikael S. Thomsen and Bent Hejgaard It is certified that error appears in the above-identified patent and that said Letters Patent is hereby corrected as shown below:

In the Claims

At Column 29, Lines 25-26 (Claim 2), delete "pharmaceutical dosage form" and insert therefor -- capsule --.

At Column 29, Lines 28-29 (Claim 3), delete "pharmaceutical dosage form" and insert therefor -- capsule --.

At Column 29, Lines 31-32 (Claim 4), delete "pharmaceutical dosage form" and insert therefor -- capsule --.

At Column 29, Lines 34-35 (Claim 5), delete "pharmaceutical dosage form" and insert therefor -- capsule --.

At Column 29, Lines 37-38 (Claim 6), delete "pharmaceutical dosage form" and insert therefor -- capsule --.

At Column 30, Line 3 (Claim 7), delete "pharmaceutical dosage form" and insert therefor -- capsule --.

At Column 30, Line 7 (Claim 8), delete "pharmaceutical dosage form" and insert therefor -- capsule --.

At Column 30, Line 10 (Claim 9), delete "pharmaceutical dosage form" and insert therefor -- capsule --.

At Column 30, Line 14 (Claim 10), delete "pharmaceutical dosage form" and insert therefor -- capsule --.

Signed and Sealed this
Third Day of January, 2023

*Katherine Kelly Vidal*

Katherine Kelly Vidal
*Director of the United States Patent and Trademark Office*

At Column 30, Lines 16-17 (Claim 11), delete "pharmaceutical dosage form" and insert therefor -- capsule --.

At Column 30, Lines 20-21 (Claim 12), delete "pharmaceutical dosage form" and insert therefor -- capsule --.

At Column 30, Lines 24-25 (Claim 13), delete "pharmaceutical dosage form" and insert therefor -- capsule --.

At Column 30, Line 29 (Claim 14), delete "pharmaceutical dosage form" and insert therefor -- capsule --.